US012681020B2

(12) United States Patent
Simon et al.

(10) Patent No.: US 12,681,020 B2
(45) Date of Patent: Jul. 14, 2026

(54) COMPOSITIONS AND METHODS FOR NK-92 CELLS EXPRESSING NATIVE CD16

(71) Applicant: ImmunityBio, Inc., San Diego, CA (US)

(72) Inventors: Barry J. Simon, San Diego, CA (US); Laurent H. Boissel, San Diego, CA (US); Prachi Jain, San Diego, CA (US)

(73) Assignee: ImmunityBio, Inc., San Diego, CA (US)

( * ) Notice: Subject to any disclaimer, the term of this patent is extended or adjusted under 35 U.S.C. 154(b) by 0 days.

(21) Appl. No.: 19/085,903

(22) Filed: Mar. 20, 2025

(65) Prior Publication Data

US 2025/0298030 A1     Sep. 25, 2025

Related U.S. Application Data

(60) Provisional application No. 63/567,784, filed on Mar. 20, 2024.

(51) Int. Cl.
| | |
|---|---|
| *G01N 33/68* | (2006.01) |
| *C07K 14/705* | (2006.01) |
| *C07K 14/735* | (2006.01) |
| *C12N 5/0783* | (2010.01) |
| *C12N 15/90* | (2006.01) |
| *G01N 33/569* | (2006.01) |

(52) U.S. Cl.
CPC ... *G01N 33/6845* (2013.01); *C07K 14/70535* (2013.01); *C12N 5/0646* (2013.01); *C12N 15/907* (2013.01); *G01N 33/56972* (2013.01); *C12N 2503/00* (2013.01); *G01N 2333/70535* (2013.01)

(58) Field of Classification Search
None
See application file for complete search history.

(56) References Cited

U.S. PATENT DOCUMENTS

| | | | | |
|---|---|---|---|---|
| 10,456,420 B2 * | 10/2019 | Lee | ................. | A61K 39/39558 |
| 10,736,921 B2 * | 8/2020 | Lee | ........................ | A61P 35/00 |
| 10,774,310 B2 * | 9/2020 | Klingemann | .... | C07K 14/70535 |
| 11,000,550 B2 * | 5/2021 | Lee | .................... | C07K 16/2887 |
| 11,207,350 B2 * | 12/2021 | Lee | .................... | C07K 16/2887 |
| 11,992,504 B2 | 5/2024 | Lee et al. | | |
| 2006/0292156 A1 * | 12/2006 | Campbell | .............. | C07K 16/32 424/155.1 |

FOREIGN PATENT DOCUMENTS

| | | |
|---|---|---|
| CN | 117355600 A | 1/2024 |
| KR | 20170131569 A | 11/2017 |

OTHER PUBLICATIONS

Klingemann, "The NK-92 cell line—30 years later: its impact on natural killer cell research and treatment of cancer" 25 Cytotherapy 451-457 (Year: 2023).*

Huang et al., "Enhanced NK-92 Cytotoxicity by CRISPR Genome Engineering Using Cas9 Ribonucleoproteins" 11 Frontiers in Immunology 1008, 1-16 (Year: 2020).*

International Search Report and Written Opinion received in PCT Application No. PCT/IB2025/052949 dated Dec. 10, 2025, 14 pages.

Monteiro, M. F. et al., "NK Cytotoxicity Mediated by NK-92 Cell Lines Expressing Combinations of Two Allelic Variants for FCGR3", Antibodies, 2024, vol. 13, article No. 55, pp. 1-25.

* cited by examiner

*Primary Examiner* — Nancy J Leith

(74) *Attorney, Agent, or Firm* — Umberg Zipser LLP; Martin Fessenmaier; Priti Phukan

(57)     ABSTRACT

A recombinant NK-92 cell has a constitutive active promotor that effects expression of native CD16, and most preferably homogenous CD16 158V. Further contemplated recombinant NK-92 cells also include a recombinant nucleic acid that encodes an intracellularly retained interleukin (e.g., IL-2 or er-IL-2), wherein the recombinant NK-92 cell will secrete no more than 5,000 pg/mL IL-2 into a culture medium. The recombinant NK-92 cells presented herein have a significantly improved signal-to-noise ratio and exhibit reduced non-ADCC cytotoxicity.

17 Claims, 25 Drawing Sheets

Specification includes a Sequence Listing.

Objective:
Create a new NK-92 cell line that expresses endogenous CD16 (FCGR3A) gene

Method : Cas9-mediated Homology Directed Repair (HDR) to reactivate the endogenous CD16 (FCGR3A) by replacing the silenced promoter with a spleen focus-forming virus (SFFV) promoter

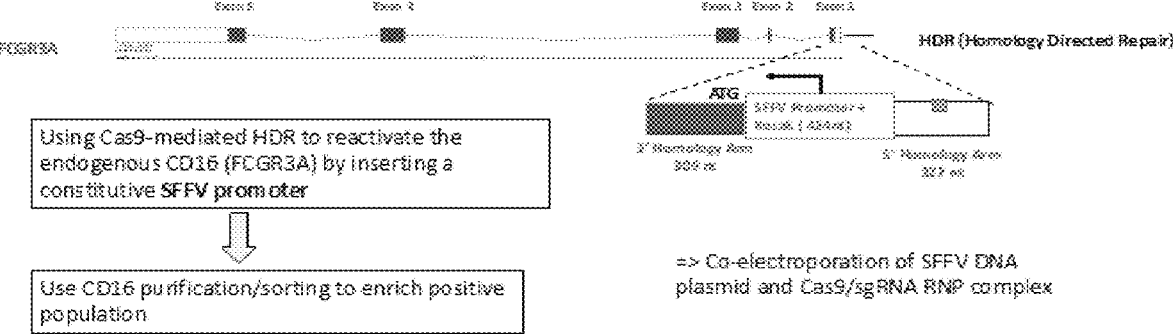

Using Cas9-mediated HDR to reactivate the endogenous CD16 (FCGR3A) by inserting a constitutive SFFV promoter

Use CD16 purification/sorting to enrich positive population

=> Co-electroporation of SFFV DNA plasmid and Cas9/sgRNA RNP complex

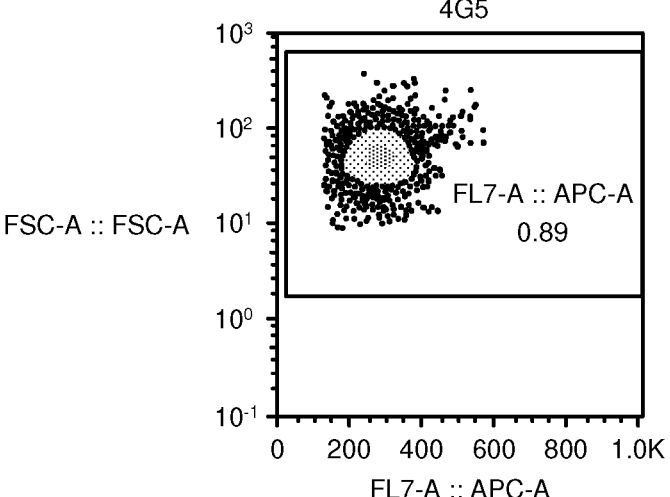
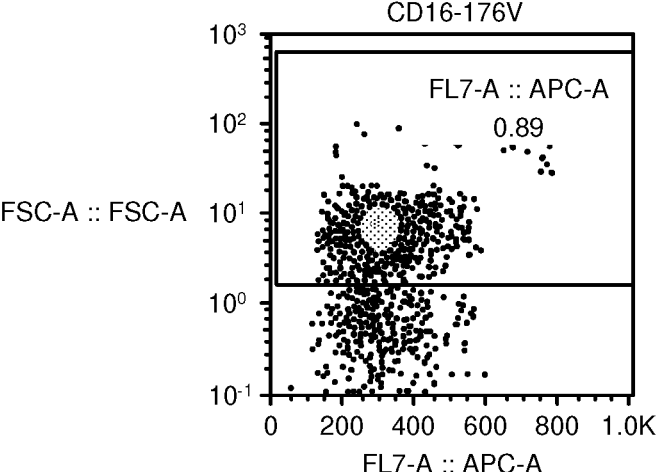
FIG. 5C

Cytotoxicity of IL-2 expressing NK-92_CD16 IL-2 IL-2/ERIL-2 clones

Cell maintained high cell viability and consistent CD16 expression in long term continuous culture
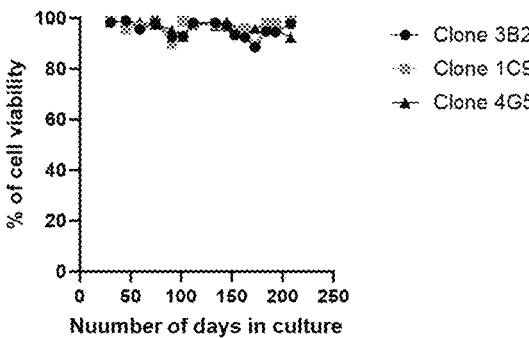
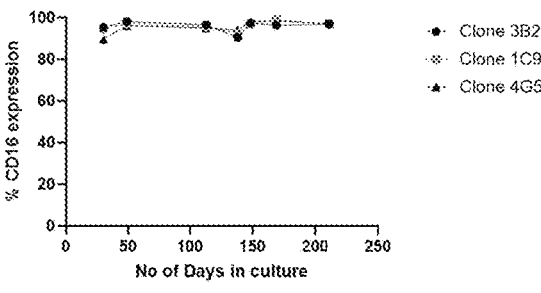
*FIG.12*

Detection of CD16A Allelic Variants by Sequencing

Determination of CD16A allelic variations in NK-92 cells
(gDNA seq)

| Sample | Analyte | Date | Reference Allele Support | Alternate Allele Support | Alt. Allele Frequency (95% CI) |
|---|---|---|---|---|---|
| NK-92 | WGS DNA | 1-Jun-15 | 48 | 34 | 41.5 (30.7, 52.9) |
| NK-92.C (= ATCC) | WGS DNA | 11-Sep-15 | 25 | 24 | 49.0 (34.4, 63.7) |
| NK-92 WT (= aNK) | WGS DNA | 11-Sep-15 | 23 | 18 | 43.9 (28.5, 60.3) |
| NK-92 FcR-IL2ER/haNK | WGS DNA | 11-Sep-15 | 25 | 15 | 37.5 (22.7, 54.2) |
| Normal PBMCs DNA | WGS DNA | 20-Aug-16 | 5 | 29 | 85.3 (68.9, 95.0) |

Reference Allele = CD16 158V

Alternate Allele = CD16 158F

Determination of CD16A allelic variations in NK-92 cells (bulk RNAseq)

| Reference sequence = CD16 158F | | | 1C9 | | | 3B2 | | | 4G5 | | | NK-92.CD16 176V | | |
|---|---|---|---|---|---|---|---|---|---|---|---|---|---|---|
| Nucleotide Position | Reference Allele | Variant Allele | Variant Count | Coverage | Variant Frequency | Variant Count | Coverage | Variant Frequency | Variant Count | Coverage | Variant Frequency | Variant Count | Coverage | Variant Frequency |
| 197 | T | A | 107 | 108 | 99.07% | 211 | 212 | 99.53% | 135 | 137 | 98.54% | n.d | n.d | n.d |
| 526 | T | G | 58 | 59 | 98.33% | 150 | 152 | 98.68% | 78 | 78 | 100% | 417 | 421 | 99.05% |

Nucleotide position 526 = 158F -> V mutation n.d. = Not Determined

All clones appear to only express the CD16 158V variant

*FIG.15*

FCGR3A gene locus gDNA

SFFV Promoter nt 526 = G

176 V

Native CD16a Promoter
(Inactive)

nt 526 = T

176 F

ATG    nt 526 = G    AAAAAA

176 V

All clones appear to only express the CD16 158V variant

Quantification of CD16 density in cell using QIFIKIT®*

NKG2D-PE MACS Column Depletion post CRISPR KO to increase NKG2D
depleted populations

42

Cytotoxicity against Ramos upon NKG2D KO

Cytotoxicity against K562 upon NKG2D KO

ADCC against Sup-B-15-Cd19-CD20+ upon NKG2D KO haNK NKG2D KO ADCC against Sup-B15-CD19-CD20+

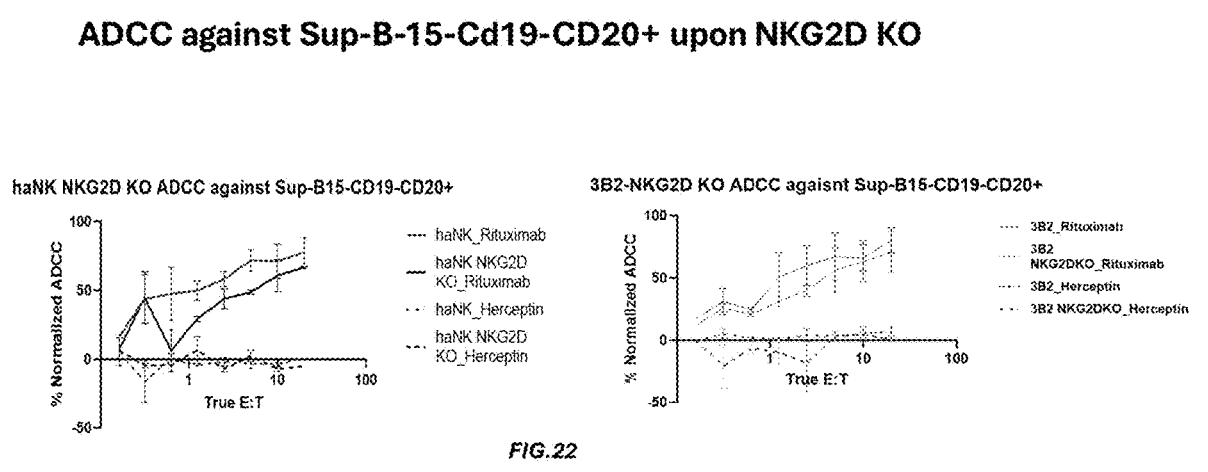

3B2-NKG2D KO ADCC agaisnt Sup-B15-CD19-CD20+

FIG.22

Cytotoxicity Characterization against K562, Ramos

SEQUENCE LISTING

Sequence total quantity: 6
SEQ ID NO: 1          moltype = DNA   length = 434
FEATURE               Location/Qualifiers
source                1..434
                      mol_type = other DNA
                      organism = synthetic construct
SEQUENCE: 1
gtaacgccat tttgcaaggc atggaaaaat accaaaccaa gaatagagaa gttcagatca   60
agggcgggta catgaaaata gctaacgttg ggccaaacag gatatctgcg gtgagcagtt   120
tcggccccgg cccggggcca agaacagatg gtcaccgcag tttcggcccc ggcccgaggc   180
caagaacaga tggtccccag atatggccca accctcagca gtttcttaag acccatcaga   240
tgtttccagg ctcccccaag gacctgaaat gaccctgcgc cttatttgaa ttaaccaatc   300
agcctgcttc tcgcttctgt tcgcgcgctt ctgcttcccg agctctataa aagagctcac   360

-continued

```
aacccctcac tcggcgcgcc agtcctccga ttgactgagt cgcccggatc ccagtgtggt   420
ggtacggggc cacc                                                      434

SEQ ID NO: 2              moltype = AA  length = 254
FEATURE                   Location/Qualifiers
source                    1..254
                          mol_type = protein
                          organism = synthetic construct
SEQUENCE: 2
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLFGSKN   180
VSSETVNITI TQGLAVSTIS SFFPPGYQVS FCLVMVLLFA VDTGLYFSVK TNIRSSTRDW   240
KDHKFKWRKD PQDK                                                     254

SEQ ID NO: 3              moltype = AA  length = 254
FEATURE                   Location/Qualifiers
source                    1..254
                          mol_type = protein
                          organism = synthetic construct
SEQUENCE: 3
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLVGSKN   180
VSSETVNITI TQGLAVSTIS SFFPPGYQVS FCLVMVLLFA VDTGLYFSVK TNIRSSTRDW   240
KDHKFKWRKD PQDK                                                     254

SEQ ID NO: 4              moltype = AA  length = 153
FEATURE                   Location/Qualifiers
source                    1..153
                          mol_type = protein
                          organism = synthetic construct
SEQUENCE: 4
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 5              moltype = AA  length = 164
FEATURE                   Location/Qualifiers
source                    1..164
                          mol_type = protein
                          organism = synthetic construct
SEQUENCE: 5
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLTGSEKDEL KDEL                    164

SEQ ID NO: 6              moltype = DNA  length = 1116
FEATURE                   Location/Qualifiers
source                    1..1116
                          mol_type = other DNA
                          organism = synthetic construct
SEQUENCE: 6
gccgggagca ggcgtgagtg tgggaaatga aggaagccct cagagaatgc tcctcccacc    60
ttgaatctca tccccagggt ctcactgtcc cattcttggt gctgggtgga tccaaatcca   120
ggagatgggg caagcatcct gggatggctg agggcacact ctggcagatt ctgtgtgtgt   180
cctcagatgc tcagccacag acctttgagg gagtaaaggg ggcagaccca cccaccttgc   240
ctccaggctc tttaattcct ggtcctgttc tatggtgggg ctcccttgcc agacttcaga   300
ctgagaagtc agatgaagtt tcaagaaaag gaaattgcta ggtgacagag gtaacgccat   360
tttgcaaggc atggaaaaat accaaaccaa gaatagagaa gttcagatca agggcgggta   420
catgaaaata gctaacgttg ggccaaacag gatatctgcg gtgagcagtt tcggccccgg   480
cccgggggcca agaacagatg gtcaccgcag tttcggcccc ggcccgaggc caagaacaga   540
tggtccccag atatggccca accctcagca gtttcttaag acccatcaga tgtttccagg   600
ctcccccaag gacctgaaat gacccctgcgc cttatttgaa ttaaccaatc agcctgcttc   660
tcgcttctgt tcgcgcgctt ctgcttcccg agctctataa aagagctcac aacccctcac   720
tcggcgcgcc agtcctccga ttgactgagt cgcccggatc ccagtgtggt ggtacggggc   780
caccatgggg ggagggggctg gggaaaggct gtttacttcc tcctgtctag tcggtttggt   840
cccttttaggg ctccggatat ctttggtgac ttgtccactc cagtgtggca tcatgtggca   900
gctgctcctc ccaactgctc tgctacttct aggtaagtca gggtctccct ggttgaggga   960
gaagtttgag atgccttggg ttcagcagag acccctttc aggctacgaa tgagactccc   1020
acgaaggggat gggaccccctc accacatcta tagctgtgga ttgagctcct aggacaagcc   1080
aagatggggc taggccggga gcaggcgtga gtgtgg                             1116
```

COMPOSITIONS AND METHODS FOR NK-92 CELLS EXPRESSING NATIVE CD16

This application claims priority to our US provisional patent application with the Ser. No. 63/567,784, which was filed Mar. 20, 2024, and which is incorporated by reference herein.

SEQUENCE LISTING

The content of the XML file of the sequence listing named 104077.0027.xml, which is 8,615 bytes in size was created on Mar. 17, 2025 and electronically submitted via EFS-Web along with the present application and is incorporated by reference in its entirety.

FIELD OF THE INVENTION

The field of the invention is recombinant nucleic acids and cells, especially as they relate to the generation of NK-92 cells that natively express high affinity CD16 and optionally intracellularly retained IL-2.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In order to test the antibody-dependent cellular cytotoxicity (ADCC)-enabling properties of a given antibody in an in vitro setting, effector cytotoxic cells that express CD16 (FCGRA3) are required, and CD16-positive NK cells obtained from peripheral blood have traditionally been used for such purpose. However, the genetic diversity between donors in terms of CD16 isoforms (e.g., 158F and 158V) and of NK-cell cytotoxic activity generates substantial variability in ADCC assays using such cells. Moreover, since the different CD16 isoforms have different affinities for binding antibodies, characterization of a particular antibody generally requires cumbersome genotyping of the donors to determine their 158 F/V zygosity. Although individuals homozygous for the high affinity isoform of the CD16 receptor (V/V) are the most likely to benefit from monoclonal antibody therapy, the majority of the general population (~80%) is either heterozygous (V/F), or homozygous for the low affinity version (F/F).

The NK-92 cell line is well suited for lab testing in that it offers a reliable source of effector cells, however, NK-92 cells do not naturally express CD16. NK-92 cells engineered to overexpress a CD16 transgene (158V or 158F) have strong ADCC capabilities and provide consistency between assays. Unfortunately, such engineered NK-92 cells are known to spontaneously kill a wide range of targets, leading to a low signal-to-noise ratio between ADCC and natural cytotoxicity background.

Therefore, to test ADCC activity of a given antibody in a model that is more readily applicable to the clinic, NK cells have been used that are engineered to express a transgene CD16 158V or 158F. However, the currently available NK-92 cells having transgenic CD16 are subject to selective pressure, and as a result CD16 expression is lost within a few weeks.

It is difficult to determine the true benefits of a given antibody by measuring ADCC activity in cells that express a transgene CD16 158V or 158F. Using NK cells isolated from the peripheral blood of human donors is a more representative alternative, but the process is generally cumbersome and expensive. Moreover, such tests will typically be at the mercy of donor-to-donor variability in NK cells quality.

Thus, even though various NK cells and methods are known in the art, all or almost all of them suffer from several drawbacks. Therefore, there remains a need for improved NK cells with predictable cytotoxicity, low non-specific cytotoxicity, and with homogenous expression of the native CD16 158V allele.

SUMMARY OF THE INVENTION

The present disclosure provides novel recombinant NK-92 cells engineered for homogenous expression of the native CD16 158V allele that have predictable cytotoxicity and low non-specific cytotoxicity. These recombinant NK-92 cells offer improved performance over conventional NK-92 cell models, including stable homogenous CD16 expression, reduced background cytotoxicity, and more predictive ADCC results, making them especially suited for preclinical testing of therapeutic antibodies.

In one aspect, the invention provides a recombinant NK-92 cell comprising a recombinant promoter sequence positioned upstream of a gene encoding a native CD16 allele, where the recombinant promoter is operably coupled to the gene to enable expression of CD16. The recombinant promoter may be a constitutive promoter, including but not limited to non-human promoter sequences, such as the spleen focus forming virus (SFFV) promoter. The recombinant promoter may replace an inactive native CD16 promoter, thereby restoring native CD16 expression in NK-92 cells.

In some embodiments, the recombinant NK-92 cell comprises the native CD16 allele which is heterozygous (both 158V and 158F variants of CD16), but the cells express only the CD16 158V variant.

The recombinant NK-92 cells of the present invention are engineered to remain viable and maintain consistent CD16 expression for at least six months, ensuring reliability and reproducibility in long-term studies and assays.

In additional embodiments, the recombinant NK-92 cells may further comprise a recombinant nucleic acid encoding an intracellularly retained cytokine, such as interleukin-2 (IL-2) or endoplasmic reticulum-retained IL-2 (er-IL-2). These cytokines are expressed in a manner that supports cell survival without substantial secretion into the culture medium, with secreted IL-2 levels maintained below 5,000 pg/mL, thereby minimizing unintended effects on co-cultured target cells during ADCC assays.

Moreover, the recombinant NK-92 cells may also comprise antibiotic resistance genes and/or reporter genes for selection and tracking purposes.

The recombinant NK-92 cells express CD16 on their cell surface, enabling binding to the Fc region of antibodies in ADCC assays. Importantly, these cells demonstrate functional ADCC activity against target cells expressing a cognate antigen when bound by an antibody, and they exhibit lower background (non-ADCC) cytotoxicity and reduced signal-to-noise ratio compared to non-recombinant parental NK-92 cells, thereby improving the accuracy and predictive value of ADCC measurements.

In another aspect, the invention provides cell lines and compositions comprising a plurality of the recombinant NK-92 cells described herein, enabling scalable production for research and industrial applications.

Further, provided are methods of testing antibodies, including therapeutic IgG antibodies for human use. The method comprises: providing a plurality of target cells expressing an antigen of interest; providing a plurality of recombinant NK-92 cells, or a cell line or composition comprising such cells; combining the target cells and recombinant NK-92 cells in the presence of an antibody that binds to the target antigen; and measuring ADCC against the target cells.

Preferably, the assay is conducted under conditions in which the target cells are not substantially exposed to cytokines secreted by NK-92 cells, avoiding cytokine-mediated artifacts. The effector-to-target (E:T) ratio of NK-92 cells to target cells may range from 0.1:1 to 50:1, including preferred sub-ranges such as 1:1 to 40:1, 5:1 to 20:1, and 10:1 to 20:1, depending on assay requirements. Notably, the method is designed to generate more predictive and accurate ADCC data than assays using NK-92 cells transgenically overexpressing high-affinity CD16.

Additionally, the invention provides methods for generating recombinant NK-92 cells, comprising: providing a NK-92 cell line; and introducing a recombinant promoter sequence upstream of a native CD16 allele, preferably via electroporation, to create the recombinant NK-92 cell.

In summary, the present disclosure provides a next-generation NK-92 cell platform for ADCC assays and other therapeutic or research uses, addressing limitations of current NK cell models by delivering consistent functional homogenous expression of the native CD16 158V allele with minimal assay interference from non-specific effects.

BRIEF DESCRIPTION OF THE DRAWING

FIG. 1 is an exemplary schematic illustration for promotor replacement in NK-92 to produce the recombinant cells according to the inventive subject matter.

FIG. 3 depicts exemplary results for ADCC against target cells expressing CD20 using haNK cells and recombinant NK-92 cells according to the inventive subject matter.

FIG. 12 depict exemplary that the recombinant NK-92 cells disclosed herein maintains high cell viability and consistent CD16 expression in long term continuous culture.

FIG. 14 depict exemplary the determination of CD16A allelic variations in NK-92 cells from DNA sequencing.

FIG. 15 depict exemplary the determination of CD16A allelic variations in NK-92 cells from RNA sequencing.

FIG. 22 depict exemplary ADCC against Sup-B-15-CD19-CD20+ upon NKG2D KO.

DETAILED DESCRIPTION

Figure 2:
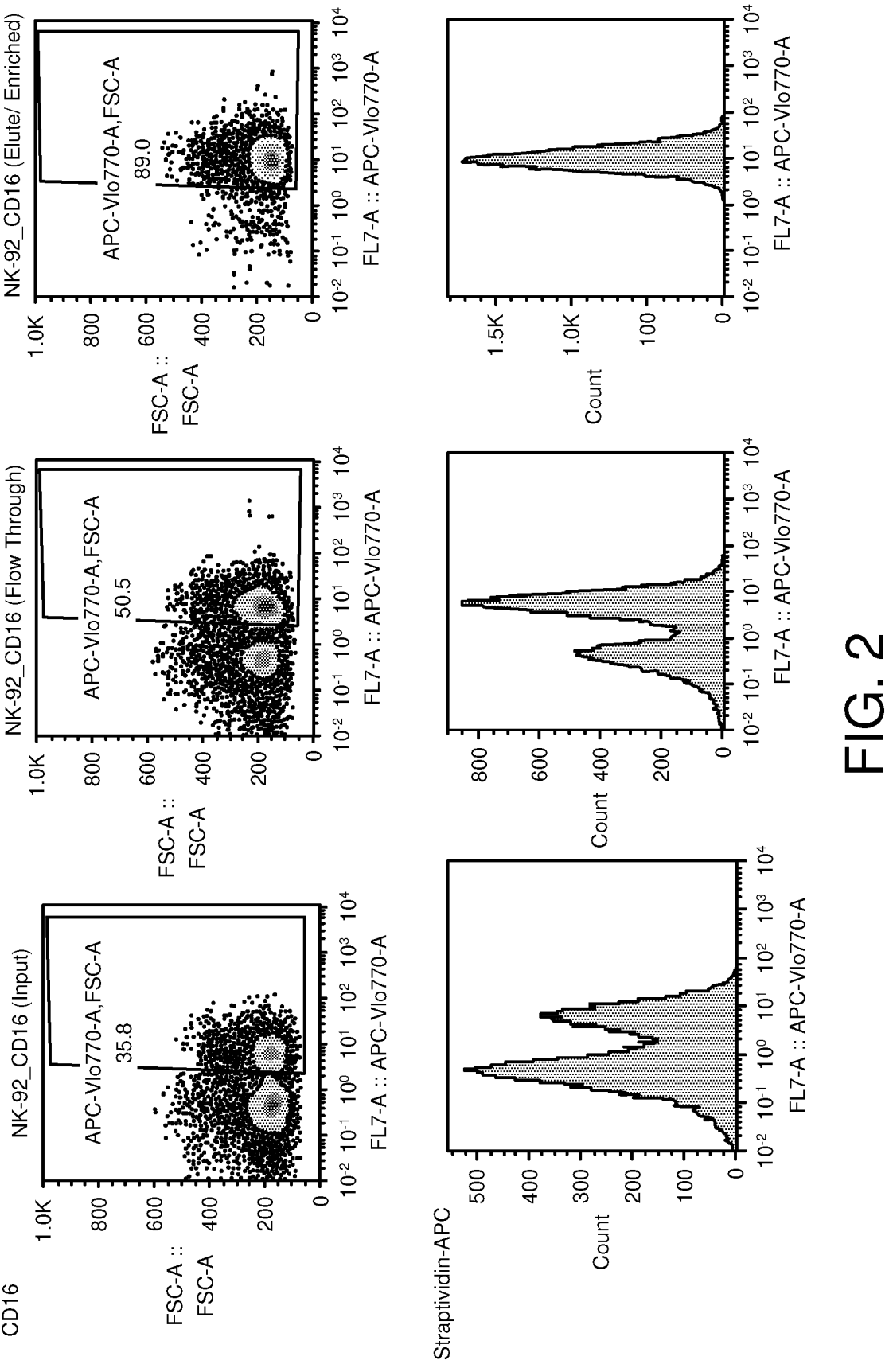
FIG. 2 depicts exemplary FACS results for cell enrichment of the recombinant cells generated according to FIG. 1.

The inventors have now discovered that NK-92 cells can be genetically modified to form cells that express endogenous (native) homogenous CD16 158V by genetically replacing the native silenced promotor sequence with a replacement promotor that is preferably constitutive. Moreover, the cells presented herein will advantageously also recombinantly express an intracellularly retained cytokine to so confer autotrophy, and most typically, the cytokine will not be secreted to a degree that would otherwise affect the behavior of a target cell (as would be the case, for example, with NK-92 MI cells that recombinantly express a secreted cytokine and that produces it in substantial quantities.

On this backdrop, the inventors devised a way to generate an NK-92 cell line that express their endogenous CD16 (FCGR3A) gene and that have a substantially improved signal-to-noise ratio for ADCC testing. Moreover, it should be recognized that the so modified NK-92 cells express only the native CD16 158V allele (but not the CD16 158F allele), and because the so modified NK-92 cells were created by inserting a promoter in front of the native gene, potential natural post-transcriptional regulations are conserved. Therefore, these cells are uniquely suited for laboratory use for discerning differences in the potency of two mAbs that would otherwise be missed when using the currently available NK-92 cells (for example, NK-92, NK-92 CI, or NK-92 MI). Viewed from a different perspective, it should be recognized that with endogenous CD16 expression as presented herein, the recombinant NK-92 cells are better suited for an ADCC assay as they will have an improved signal-to-noise ratio (due to lower non-specific cytotoxicity).

Where desired, these cells can also be subjected to lentiviral transduction to express a secreted or non-secreted version of the cytokine IL-2, along with a luciferase reporter and a puromycin antibiotic resistance gene. IL-2 expressing NK-92 are highly advantageous in culture as they do not require addition of exogenous cytokine. However, high level of IL-2 secretion (such as displayed by NK-92.MI cells) is not desirable as it could interfere with in vitro and in vivo assays.

In addition to the expression of native homogenous CD16 158V (or as an alternative), the inventors further contemplate that (i) adding inhibitory KIRs such as KIR2DL1/2 would be one way to inhibit the balance of native activating receptors while not affecting the ability of receptors such as FcGRIIIa (as well as CARs) to activate killing. In such a setting, the signal-to-noise ratio would be increased; (ii) knock out expression of the NKG2D activating receptor can be performed. This would also increase the signal-to-noise ratio would be favorably pushed towards signal while not affecting the ability of receptors such as FcGRIIIa (as well as CARs) to activate killing.

The term "homogenous expression" or "homogenous CD16 158V" as used herein refers to selective expression of the 158V allele of CD16, but not the 158F allele. In an embodiment, "homogenous expression" or "homogenous CD16 158V" refers to selective expression of less than 10%, or less than 5%, or less than 1% of the 158F allele, and further refers to selective expression of more than 90%, or more than 95%, or more than 99% of the 158V allele.

Moreover, when making the cells according to the inventive subject matter, it should be recognized that clonal selection will allow preparation of tailored modified cells that have a desirably (and selectably) low level of test interference by cytokines otherwise encountered (either needed in heterotrophic cell lines or leaked from autotrophic cell lines) and cell lines with desirably (and selectably) high signal-to-noise ratio. In this context it should be noted that IL-2 or IL15 secretion in the medium can be kept below 5,000 pg/mL, or 3,000 pg/mL, or 1,000 pg/mL, and even lower. As such, contemplated cells will not interfere with in vivo effector cells and not create systemic effects on lab animals (e.g., systemic IL-2 toxicity in mice).

Finally, it is contemplated that the cells as presented herein will have a viability (and even capacity to proliferate) that is sufficiently long to allow commercial use. For example, unfrozen cells will have minimum viability of at least 2 weeks, or at least 4 weeks, or at least 7 weeks, or at least 3 months, or at least 6 months, and even longer. Moreover, the cells presented herein can be frozen for several weeks or months and thawed while maintaining their cytotoxic and ADCC properties.

In still further contemplated aspects, the inventors also consider additional genomic alternations to push the balance between activating and inhibiting receptors towards less activation (e.g., via knock out expression of the NKG2D activating receptor). This would also increase the signal-to-noise ratio would be favorably pushed towards signal while not affecting the ability of receptors such as FcGRIIIa (as well as CARs) to activate killing.

As detailed throughout this disclosure, provided herein are recombinant NK-92 cells engineered to include a recombinant promoter sequence positioned upstream of a gene encoding a native CD16 allele. This recombinant promoter sequence is operably linked to the CD16 gene, thereby enabling and driving the expression of native CD16 on the NK-92 cell surface. Preferably, the recombinant promoter sequence is a constitutive promoter, allowing for continuous gene expression under standard conditions, and most preferably, this constitutive promoter is a Spleen Focus Forming Virus (SFFV) promoter. The SFFV promoter sequence contemplated herein has the sequence according to SEQ ID NO:1.

In certain embodiments, the recombinant promoter sequence replaces a non-functional or inactive native promoter sequence, effectively restoring native CD16 gene expression.

The recombinant NK-92 cell disclosed herein contains a native CD16 allele that is naturally heterozygous, meaning it carries both the 158F (SEQ ID NO:2) and 158V (SEQ ID NO: 3) variants. However, unexpectedly, the inventors found that incorporation of the recombinant promoter leads to preferential expression of only the 158V variant on the cell surface, resulting in homogenous expression of the 158V allele, while the 158F allele is not expressed. This selective expression of CD16 158V was surprising and offers advantages for therapeutic applications that require high-affinity CD16-mediated functions.

Additionally, it was found that the recombinant NK-92 cells described in this disclosure remain viable for a prolonged period of at least six (6) months or up to 200 days, demonstrating no loss of cell health or function during this time. Furthermore, these cells exhibit stable and consistent expression of CD16 throughout this duration, confirming the reliability of the recombinant promoter system to maintain CD16 expression long-term. CD16 expression is maintained without a selection pressure.

In some embodiments, the recombinant NK-92 cell disclosed herein may additionally comprise a recombinant nucleic acid molecule encoding an intracellularly retained cytokine, which enhances the cell's function and viability. Preferably, this intracellularly retained cytokine is interleukin-2 (IL-2). In specific embodiments, the IL-2 protein is engineered to be expressed with a signal peptide sequence that directs the IL-2 to the endoplasmic reticulum (ER), thereby producing ER-retained IL-2 (erIL-2).

The localization of IL-2 to the ER enables intracellular accumulation of IL-2 at levels sufficient to sustain autocrine signaling, which supports NK-92 cell growth and survival without significant extracellular secretion of IL-2. This approach prevents undesired paracrine effects and systemic cytokine exposure. See Konstantinidis et al., "Targeting IL-2 to the endoplasmic reticulum confines autocrine growth stimulation to NK-92 cells," *Exp. Hematol.* 2005 February; 33 (2): 159-64, as well as WO2019226708 and WO2020028656, each incorporated herein by reference in their entirety.

A representative IL-2 polypeptide sequence is provided in SEQ ID NO:4, and a representative erIL-2 polypeptide sequence is shown in SEQ ID NO:5. Preferably, when cultured under standard conditions, the recombinant NK-92 cells secrete no more than 5,000 pg/mL of IL-2 into the culture medium, ensuring minimal extracellular cytokine levels while maintaining robust autocrine signaling for sustained activity.

In additional embodiments, the recombinant NK-92 cell may also harbor a recombinant nucleic acid encoding an antibiotic resistance gene and/or a reporter gene. The antibiotic resistance gene, confers resistance to antibiotics like puromycin and serves as a positive selection marker, enabling selective growth of genetically modified cells under antibiotic pressure.

Furthermore, a reporter gene may be included to facilitate the tracking and quantification of gene expression or regulatory sequence activity. Such reporter genes typically encode detectable signals, such as fluorescent proteins (e.g., GFP) or enzymes (e.g., luciferase), providing an essential tool for monitoring transgene expression and functional studies of the recombinant cells.

Functionally, the recombinant NK-92 cells described herein are designed to mediate antibody-dependent cellular cytotoxicity (ADCC) against target cells that express a specific antigen. In this context, the target antigen is recognized and bound by an antibody, which in turn engages the CD16 receptor (expressed on the recombinant NK-92 cell surface), triggering ADCC and subsequent target cell lysis.

Importantly, relative to non-recombinant NK-92 cells (e.g., ATCC CRL-2407), the recombinant NK-92 cells of the present disclosure demonstrate a reduced signal-to-noise ratio during ADCC assays, indicating more specific and efficient cytotoxic activity with minimized background effects. Furthermore, these recombinant NK-92 cells exhibit reduced non-ADCC (off-target) cytotoxicity, enhancing the safety and selectivity of their therapeutic potential compared to unmodified NK-92 cells. This could be due to the polymorphism within the nucleic acid encoding CD16, which results in 197T to 197A. With this mutation, there is reduced spontaneous cytotoxicity which in turn improves the signal to noise ratio.

Also provided herein is a cell line comprising a population of recombinant NK-92 cells as described throughout this disclosure, which can be stably maintained and expanded for research and therapeutic applications.

Further provided is a composition comprising a plurality of recombinant NK-92 cells, formulated for use in various applications, including but not limited to immunotherapy, adoptive cell transfer, and preclinical research.

In another aspect of the present disclosure, provided herein is a method for evaluating the activity and efficacy of an antibody, particularly for therapeutic use, through an antibody-dependent cellular cytotoxicity (ADCC) assay. The method comprises: (1) Providing a population of target cells that express a specific antigen of interest; (2) Providing a population of recombinant NK-92 cells, as described throughout this disclosure, which are genetically engineered to express a native CD16 allele under the control of a recombinant promoter; (3) Combining the target cells and recombinant NK-92 cells in the presence of an antibody capable of specifically binding to the antigen expressed on the target cells; and (4) Measuring the ADCC activity directed against the target cells to evaluate the functional activity of the antibody.

In certain embodiments, the antibody to be tested is an IgG isotype intended for therapeutic use in humans. Preferably, the target cells are not substantially exposed to cytokines secreted by the recombinant NK-92 cells, such that the measured cytotoxicity primarily reflects ADCC rather than cytokine-mediated effects.

In various preferred embodiments, the ratio of recombinant NK-92 effector cells to target cells is selected to optimize assay sensitivity and specificity. Suitable effector-to-target (E:T) cell ratios include, but are not limited to, ratios between 0.1:1 and 50:1, or between 1:1 and 40:1, or between 5:1 and 20:1, or between 10:1 and 20:1.

Advantageously, the disclosed method generates results that are more predictive of in vivo human responses than comparable assays using NK-92 cells engineered to express a transgene encoding a high-affinity CD16 variant. Thus, the method enables more accurate assessment of antibody candidates in a preclinical setting.

In another aspect, also provided herein is a method for producing a recombinant NK-92 cell useful for ADCC-based assays and other applications. The method comprises: (1) Obtaining an NK-92 cell line, such as a cell line deposited with the American Type Culture Collection (ATCC) under Deposit No. CRL-2407; and (2) Introducing into the NK-92 cell a recombinant promoter sequence positioned upstream of a gene encoding a native CD16 allele, thereby enabling controlled expression of CD16 and generating a recombinant NK-92 cell with optimized CD16 expression; and wherein the recombinant promotor sequence is operably coupled to the gene to thereby enable expression of the native CD16.

Preferably the recombinant nucleic acid comprising the SFFV promoter sequence is introduced or delivered to the NK-92 cell via electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.).

The recombinant NK-92 cells produced by this method are suitable for use in antibody functional assays, including ADCC measurements, and provide advantages over existing NK-92 models.

The examples below are intended to further illustrate certain aspects of the compositions and methods described herein and are not intended to limit the scope of the claims.

Example 1

NK-92 cells (whether wild type or NK-92.CI cells) were electroporated with a DNA construct encoding the spleen focus-forming virus (SFFV) promoter with a Kozak sequence flanked with DNA sequences homologous to the region of the FCGR3A gene overlapping the translational start codon (ATG), along with ribonucleoparticle complexes (RNPs) formed by Cas9 protein and guide RNA molecules targeting the genomic region immediately upstream of the FCGR3A gene translational start codon. Through homologous recombination, the SFFV promoter and Kozak sequence are integrated directly upstream of the FCGR3A gene translational start codon and constitutively drives expression of the native CD16a protein. A schematic illustration for this is shown in FIG. 1.

Figure 3:
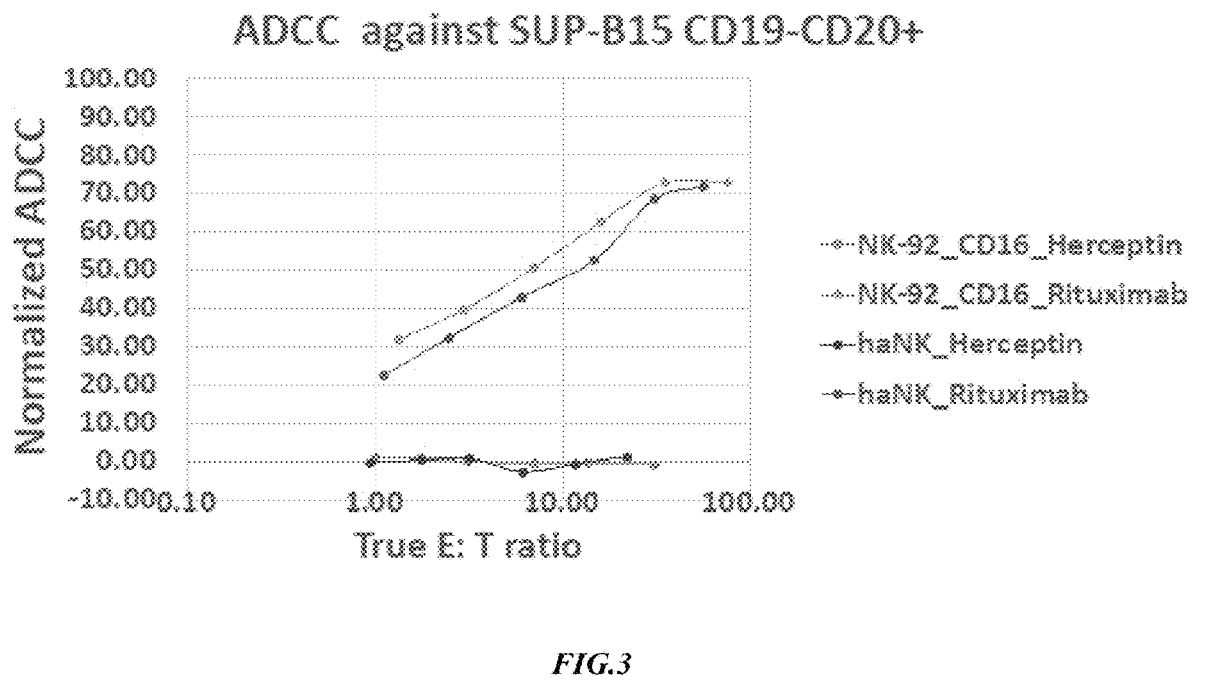

After a period of recuperation, the electroporated cells were screened for CD16 expression by flow cytometry, and CD16-positive cells were isolated by FACS or by several rounds of immunomagnetic column enrichment. Exemplary results for this screening and isolation are depicted in FIG. 2. Purified CD16-expressing NK-92 cells were then tested and performed strong in an ADCC test as can be seen from FIG. 3. Notably, the recombinant cells performed comparably to aNK cells expressing a high affinity CD16 158V transgene (haNK cells (see e.g., *Oncotarget* 2016 Dec. 27; 7 (52): 86359-86373)).

Figure 4:
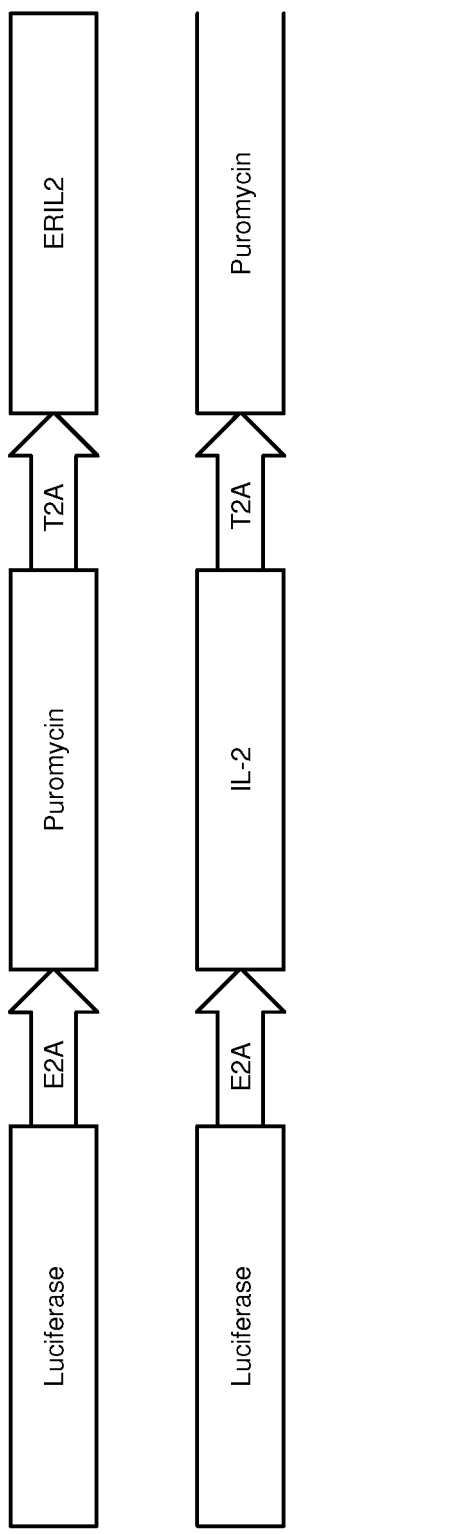
FIG. 4 depicts exemplary lentiviral polycistronic transgenes used for transfection of the recombinant NK-92 cells according to the inventive subject matter.
Figure 5A:
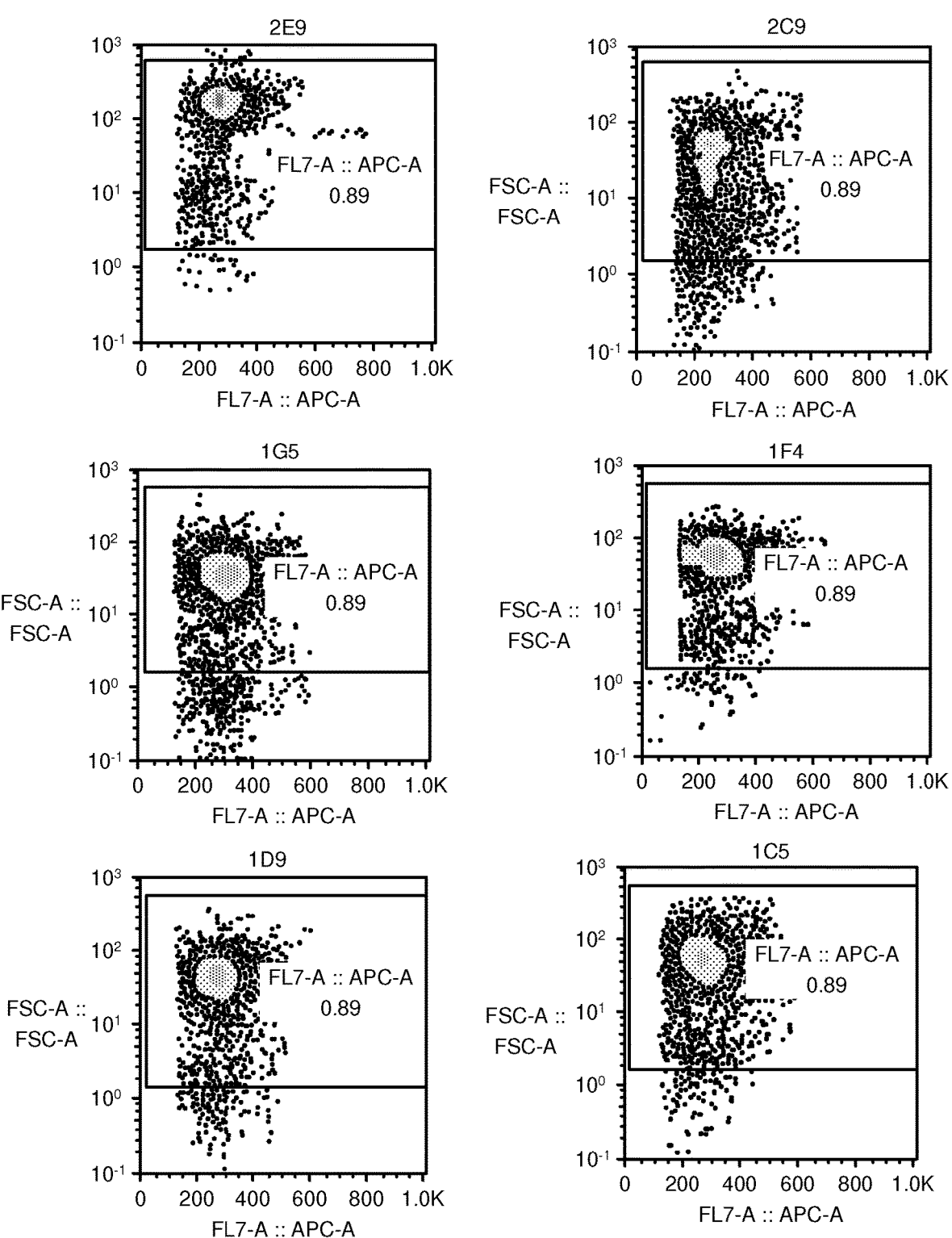
FIG. 5 depicts exemplary FACS results for expression of CD16 in selected clones after limiting dilution cloning.
Figure 5B:
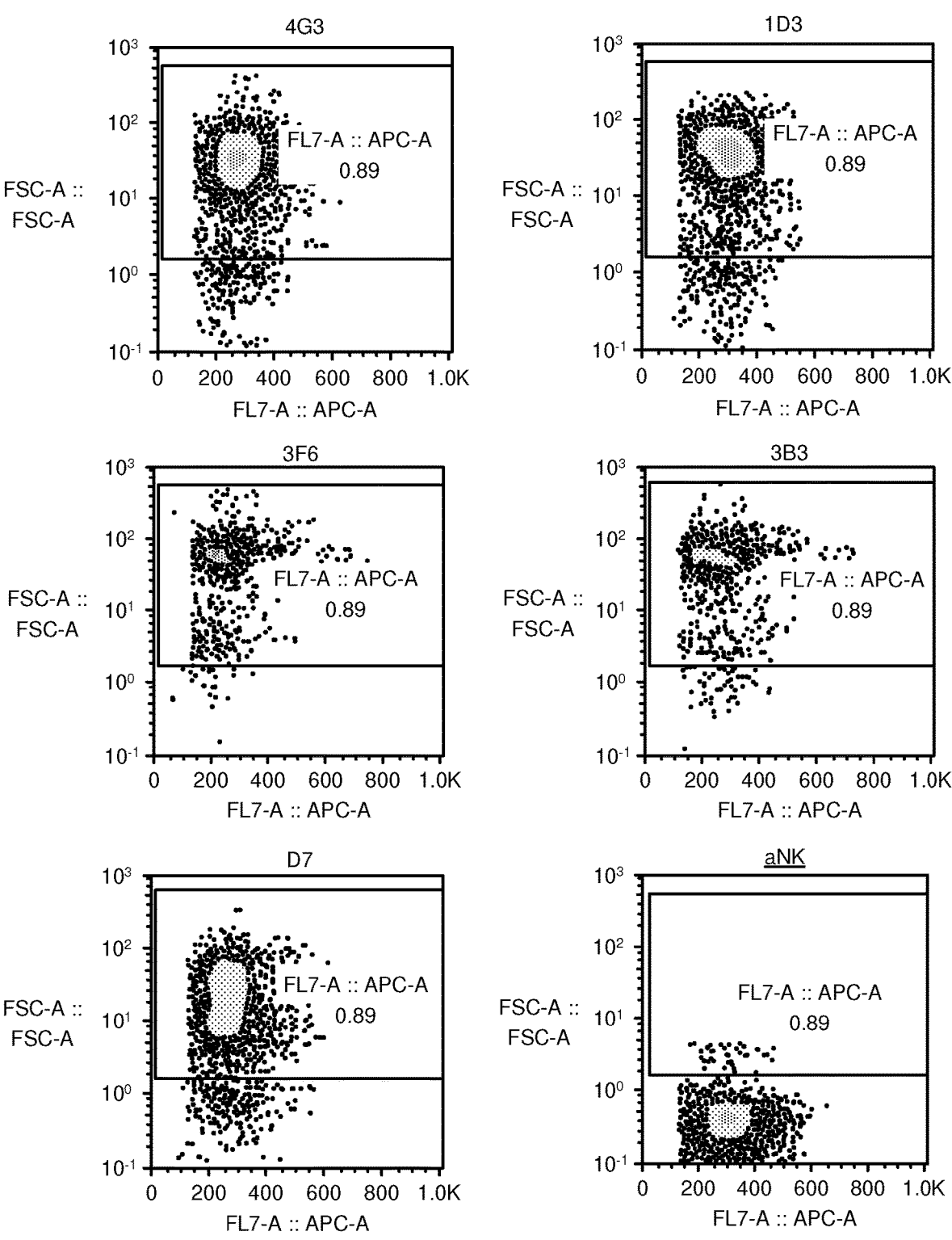

Purified CD16-expressing NK-92 cells were transduced with lentiviral vectors encoding a polycistronic transgene that drives co-expression of a Luciferase reporter protein, a puromycin resistance protein, and the cytokine IL-2 in a secreted or non-secreted (ERIL2) form. The three proteins are separated by 2A sequences and are organized in the following orders from 5' to 3' as is shown in FIG. 4. In case 1) ERIL-2 was placed in third position so that the ER-retention signal is not fused to any 2A peptide that may interfere with its function. In case 2) IL-2 is placed in second position, a position that has been shown to yield the lowest amount of peptide release and fused to a 2A peptide at its C-terminus, which is likely to interfere with its function. Both characteristics were intended to decrease the overall amount and activity of secreted IL-2. Transduced cells were selected in the presence of puromycin and in the absence of IL-2. Selected, transduced CD16-expressing NK-92 cells underwent one round of limiting dilution cloning. Several surviving clones were expanded and screened for CD16 expression and their natural cytotoxic properties against the K562 cell line. A number of clones displayed markedly decreased natural cytotoxicity compared to the parental NK-92 wild-type cell line, and exemplary results are shown in FIG. 5.

Figure 6:
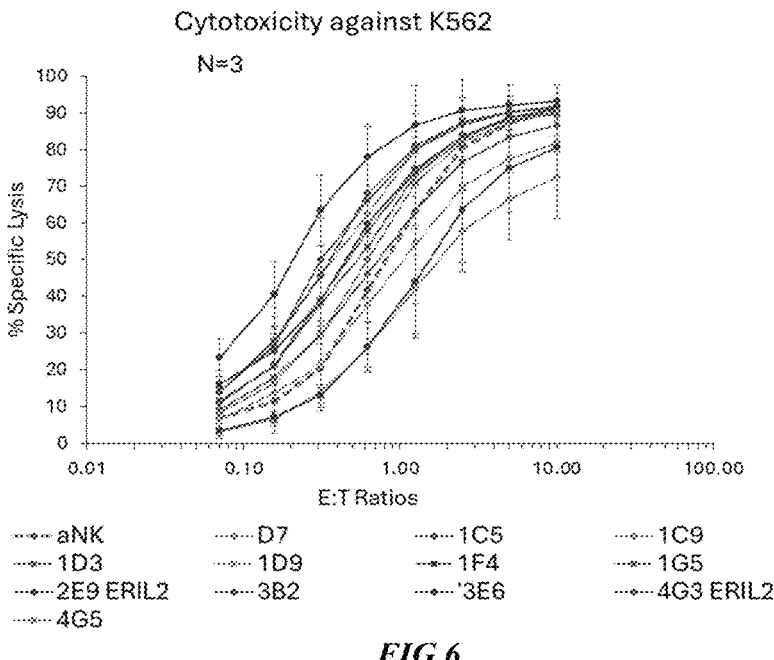
FIG. 6 depicts exemplary cytotoxicity results of aNK cells and selected clones of FIG. 5 against target cells.
Figure 7:
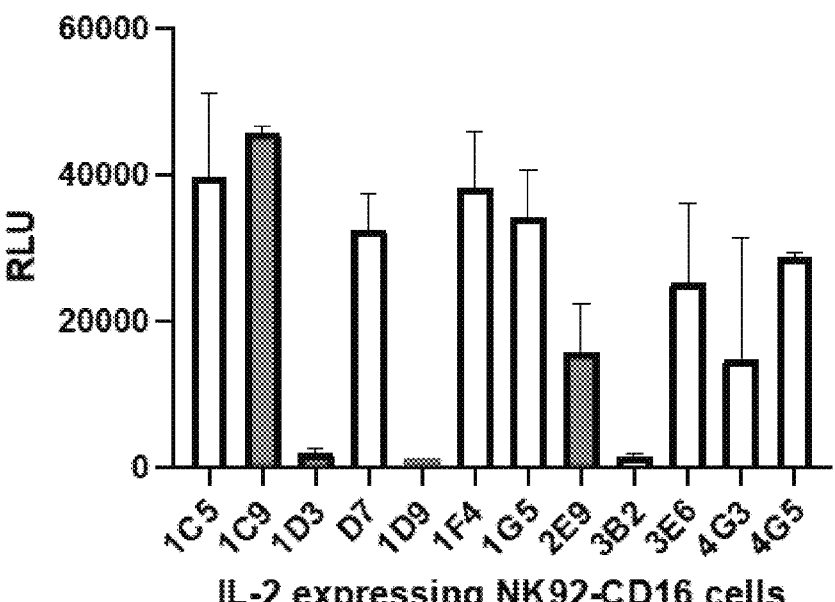
FIG. 7 depicts exemplary luciferase expression results of selected clones of FIG. 5.

As will be readily appreciated, the Luciferase and puromycin sequences were used for culture purification in the case of puromycin and in the case of luciferase, for bioluminescence that can be useful for in vivo imaging or for in vitro proliferation assays. Despite the fact that Luciferase and IL-2 are both encoded in the same viral transgene, transduced CD16-expressing NK-92 clones displayed variable luciferase expression while being able to grow well in absence of IL-2, and exemplary results are shown in FIG. 6 and FIG. 7.

Figure 8:
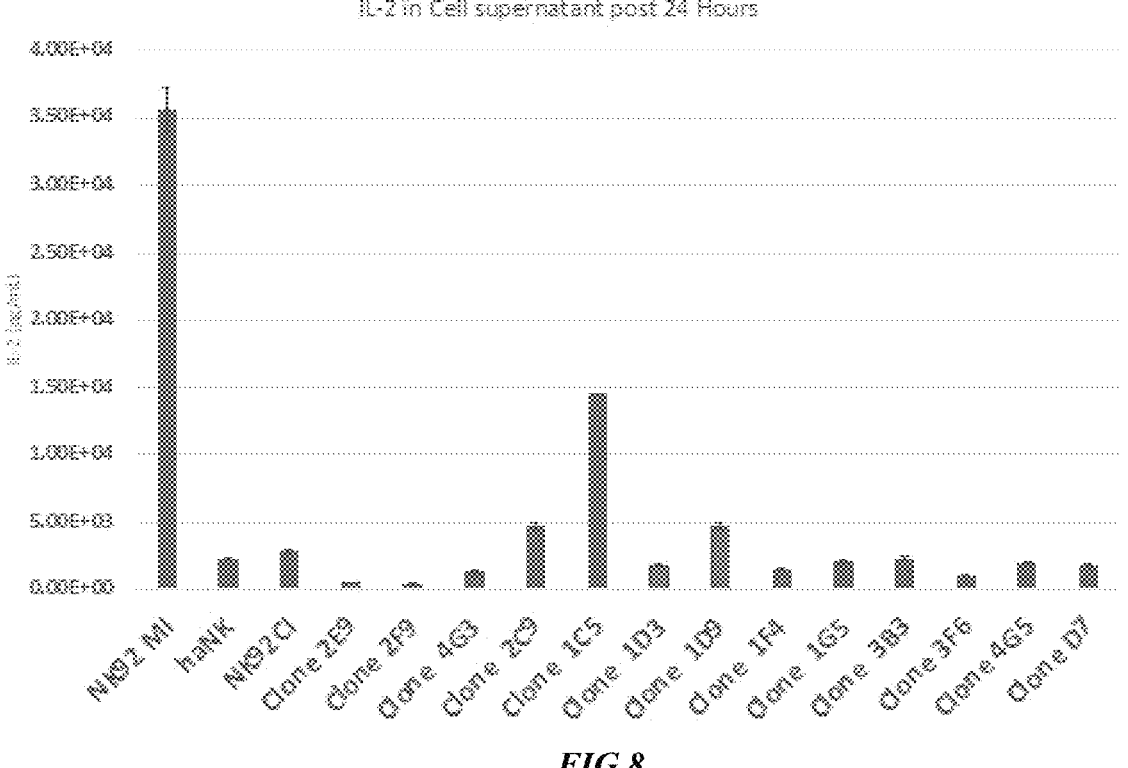
FIG. 8 depicts exemplary results for IL-2 release into the medium of selected clones of FIG. 5.
Figure 9:
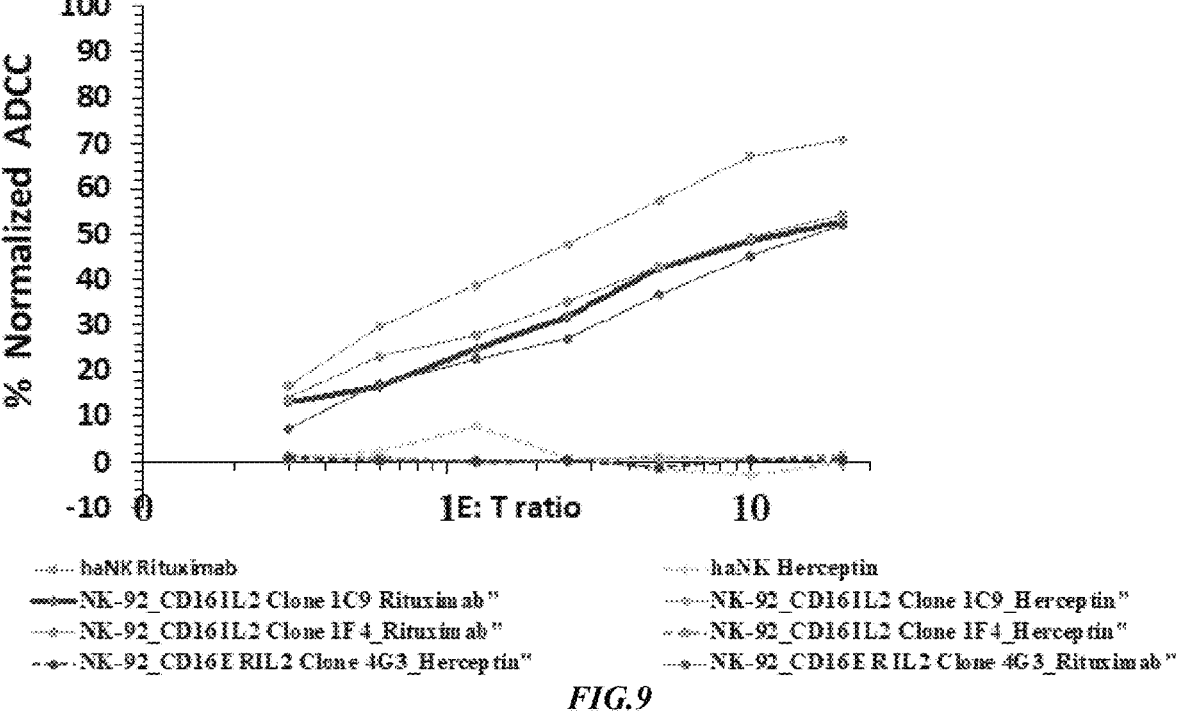
FIG. 9 depicts exemplary results for ADCC against target for selected clones of FIG. 5 with target specific and non-target specific antibodies.

Notably, transduced CD16-expressing NK-92 clones with low natural cytotoxicity background maintained their ability to perform efficiently in ADCC as can be seen from FIG. 8. Here, average IL-2 expression in clones ranges from 455 pg/mL to 14,500 pg/mL which is equivalent to 7.7 IL-2 units (U) to 256 IL-2 U; NK-92 MI have high levels of IL-2~35, 000 pg/mL corresponds to ~600 U of IL-2. Clones with less cytotoxicity compared to NK-92 are shown in red. (Note: 1 μg IL-2=16,900 Units of IL-2).

Figure 10:
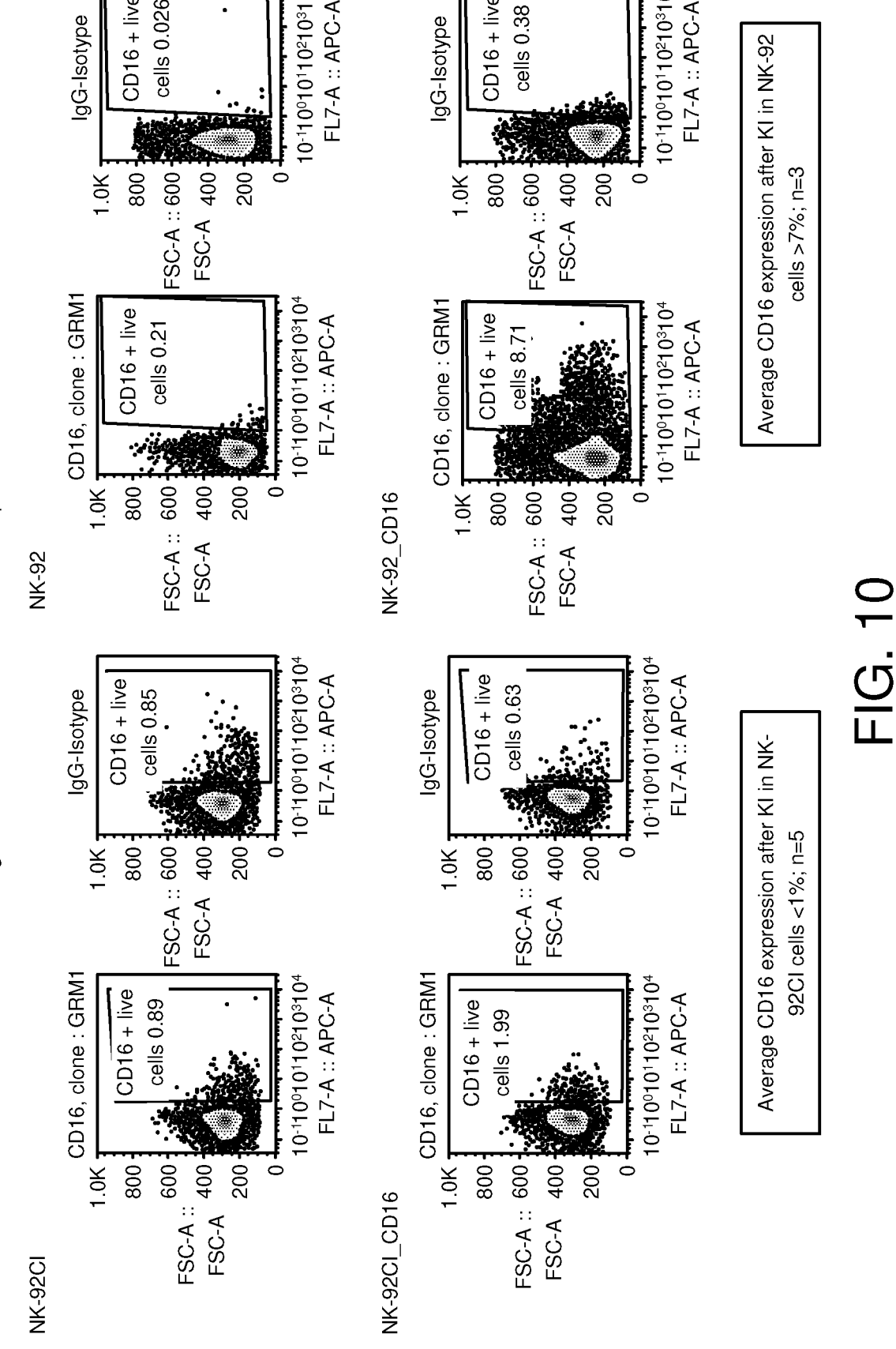
FIG. 10 depict exemplary FACS results for comparative transfection of NK-92CI cells.
Figure 11:
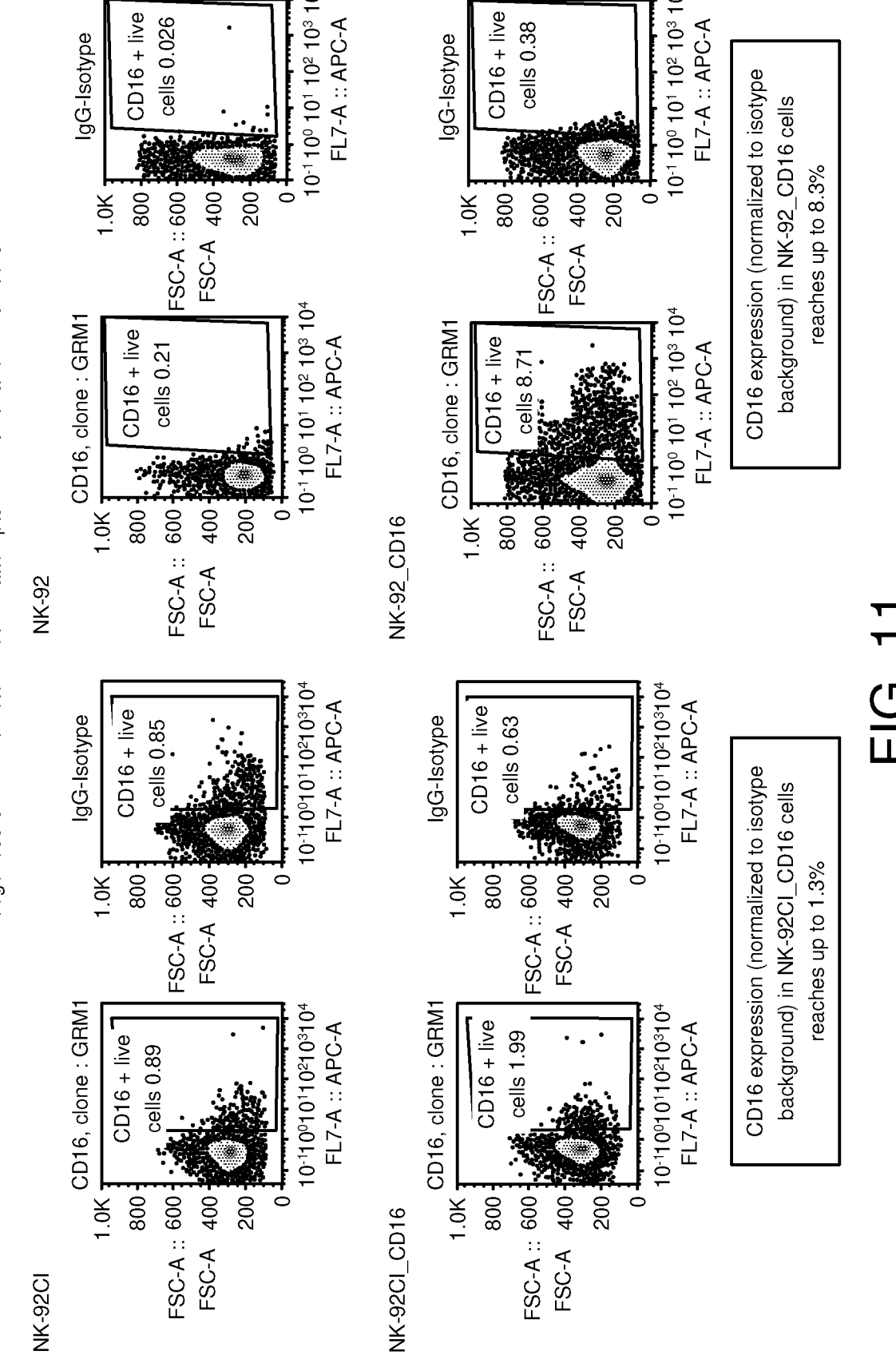
FIG. 11 depict exemplary FACS results for comparative transfection of NK-92CI cells.

While some of the methods used employed standard practices, it should be noted that the results were not readily predictable. In particular, the promotor sequence didn't work in an earlier model to fully express CD16, while it did work poorly in NK-92 CI cells. Consequently, the inventors assumed that poor performance could also be expected in wildtype NK-92 cells. FIG. 10 and FIG. 11 provide exemplary transfection results for NK-92CI cells (which did also not work in a reference cell line: HK293T). Unexpectedly, however, the inventors succeeded in generating the modified NK-92 cells as described herein with superior characteristics as shown herein.

Example 2: High Cell Viability and Consistent CD16 Expression

The inventors performed cell viability experiments on the modified recombinant NK-92 cells having the SFFV promoter. They found that following a freeze-thaw process, only a subset of the selected NK-92 CD16 IL2$^+$ clones survived, which were clones 1C9, 4G5, and 3B2. These surviving clones were subsequently characterized for cell viability and stability of CD16 expression under long-term culture conditions. Specifically, cell health was assessed by measuring cell viability every two weeks throughout the six-month period. Furthermore, CD16 expression was monitored every two weeks throughout the six-month period. The results are shown in FIG. 12. The inventors found that over the monitoring period of six months, all three clones exhibited sustained high cell viability and consistent CD16 expression without any detectable loss. Notably, this stability was maintained without the need for selection pressure, demonstrating the robustness and adaptability of these engineered clones. The term "high cell viability" refers to cell viability of at least 80%, or preferably at least 90%, more preferably at least 95%, and most preferably up to 100%. The term "consistent CD16 expression" refers to CD16 expression that does not decrease over time. For example, as shown in FIG. 12, CD16 expression of the modified NK-92 cells having the SFFV promoter exhibit a reasonably stable CD16 expression over the entire testing period of over 200 days, varying no more than about 20% at any given time as compared to initial expression levels.

Thus, the inventors unexpectedly found that the insertion of the SFFV immediately upstream of the FCGR3A gene translational start codon leads to high cell viability and drives the stable and consistent expression of CD16 throughout the life of the modified recombinant NK-92 cells.

Example 3: Expression of the CD16 158V Variant

As discussed previously, the native CD16 gene in NK-92 cells typically encode both the 158V and 158F variants of CD16 (corresponding to position 176 in SEQ ID NO:2 and SEQ ID NO: 3 of the full-length form of the CD16 polypeptide comprising the signal sequence). However, as the native CD16 promoter is inactive, there is no detectable transcription, and no mRNA reads. This is shown in top panel of FIG. 13. Because NK-92 cells do not express the CD16 Fc receptor, they are not capable of NK-mediated ADCC lysis of tumor cells employing monoclonal antibodies (MAbs) of the immunoglobulin G1 (IgG1) isotype.

Figure 13:
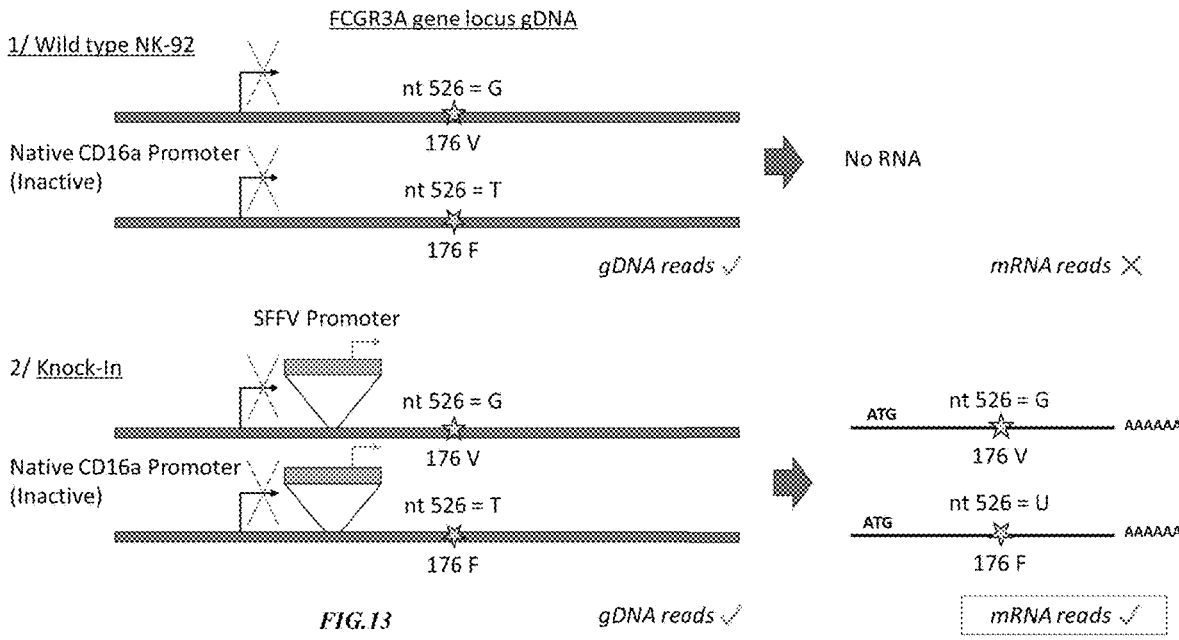
FIG. 13 depict exemplary the detection of CD16A allelic variants by sequencing.

The inventors activated the native CD16 gene in the presently disclosed engineered NK-92 clones by placing a SFFV promoter upstream of the CD16 gene (bottom panel of FIG. 13). It was expected that the activation of the native CD16 gene would lead to heterozygous expression of both the 158V and 158F variants. This belief was because NK92 cells typically possess both the 158V and 158F variants of CD16, which led to the engineering of the haNK (high affinity NK) cells to express the CD16 high affinity FcγRIIIa (158V) receptor. See Jochems C. et al., *Oncotarget.* 2016; 7:86359-86373. This was further verified via DNA sequencing which showed that the two alleles (158V and 158F) are in approximately 1:1 ratio (FIG. 14).

Figure 16:
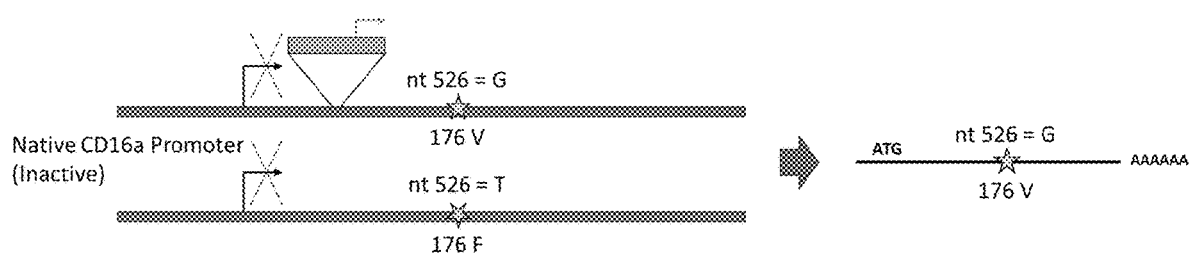
FIG. 16 depict exemplary RNAseq results.

Unexpectedly, however, Bulk RNA sequencing analysis, revealed that the engineered clones disclosed herein (with the SFFV promoter) exclusively expressed the 158V allele but not the 158F allele. This surprising result is shown in FIG. 15 and FIG. 16, where the inventors surprisingly found from sequencing data that that all engineered clones (1C9, 3B2, 4G5) exclusively expressed the CD16 158V allele, with no detectable expression of the 158F variant. This surprising result suggests a selective activation or stabilization of the 158V form in the presently disclosed modified recombinant NK-92 cells.

The CD16 158V allele in NK-92 cells confers enhanced NK-mediated ADCC lysis of tumor cells employing antibodies of the IgG1 isotype as compared to the CD16 158F allele. See Jochems C. et al., *Oncotarget.* 2016; 7:86359-86373. Thus, the presently disclosed modified recombinant NK-92 cells having a SFFV promoter upstream of the CD16 gene confers enhanced ADCC functionality, offering a novel and advantageous approach for therapeutic and/or diagnostic and testing applications.

Additionally, the inventors have identified a mutation at position 197 of CD16, resulting in the expression of the L66H mutation. This mutation has been associated with decreased spontaneous cytotoxicity without affecting ADCC (Grier et al., Human Immunodeficiency-Causing Mutation Defines CD16 in Spontaneous NK Cell Cytotoxicity, *J.*

*Immunol,* 1999). Thus, the presently disclosed recombinant NK-92 cells have reduced spontaneous cytotoxicity, thereby improving the signal to noise ratio when the ADCC of an antibody candidate is tested. Compare with Binyamin et al. *J Immunol.* 2008; 180 (9): 6392-6401, and US20060292156, each of which are incorporated by reference herein in its entirety.

Example 4: CD16 Density

Figure 17:
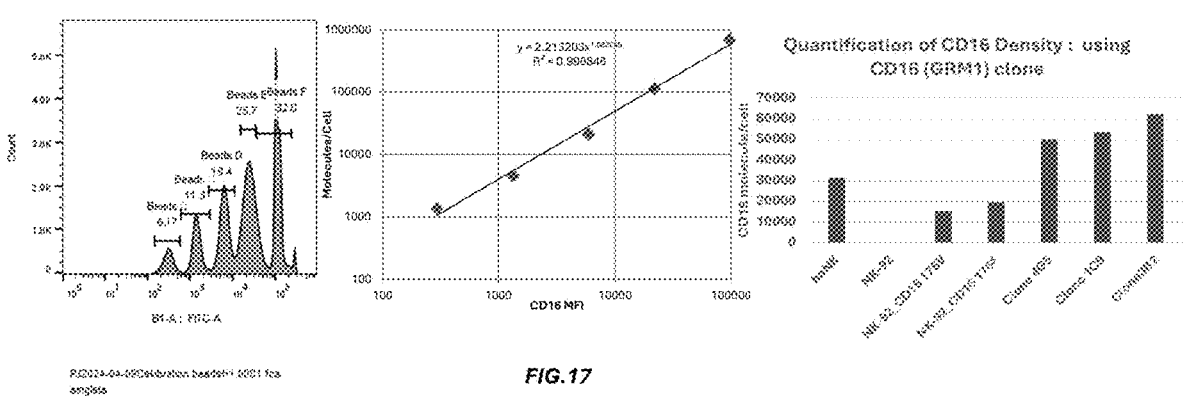
FIG. 17 depict exemplary quantification of CD16 density in the cell.

The inventors quantified the CD16 density in the engineered clones (1C9, 3B2, 4G5) using a Qifikit assay. The Qifikit assay quantifies surface protein expression by correlating fluorescence intensity to known antibody-binding capacities, thereby enabling the inventors to measure CD16 molecules per cell. The results, shown in FIG. 17, demonstrated that these clones expressed higher levels of CD16 compared to the cells disclosed in Grier et al, The *Journal of Clinical Investigation,* Volume 122 Number 10 Oct. 2012, which were generated via retroviral transduction and maintained a higher CD16 expression level compared to haNK cells, which were created using a non-viral approach. This finding highlights the superior stability and expression efficiency of the presently disclosed engineered clones.

Example 5: NKG2D Knockout Data

Figure 18:
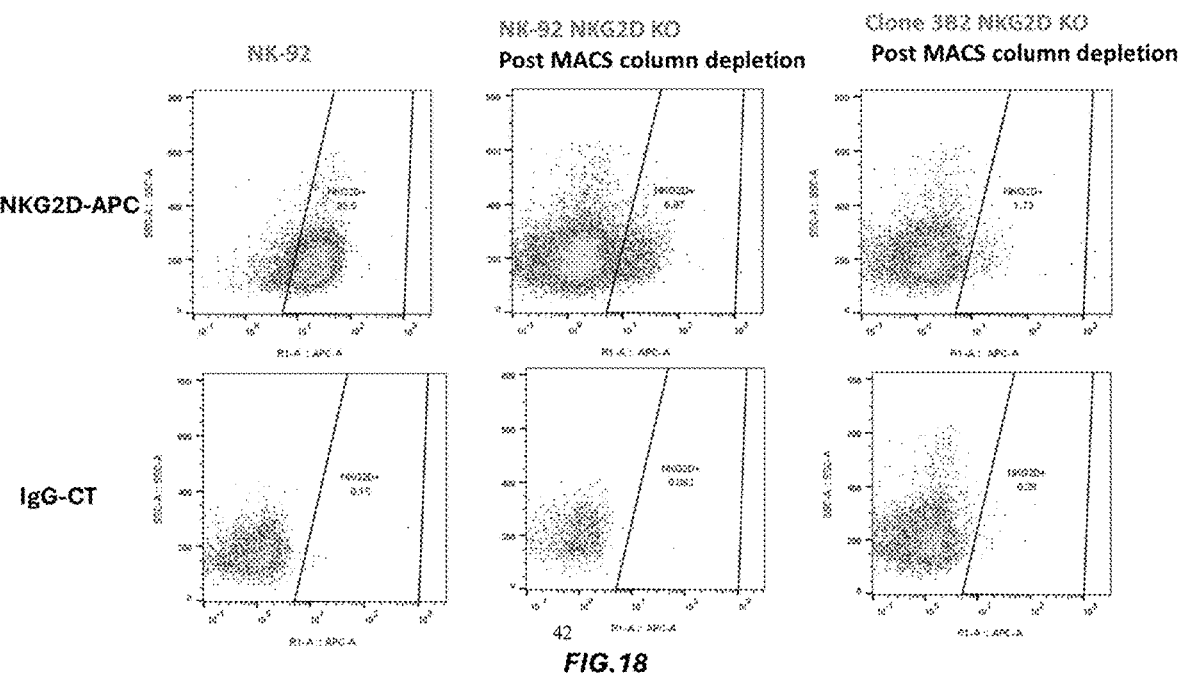
FIG. 18 depict exemplary NKG2D-PE MACS Column Depletion post CRISPR Knock Out (KO) to increase NKG2D depleted populations.
Figure 19:
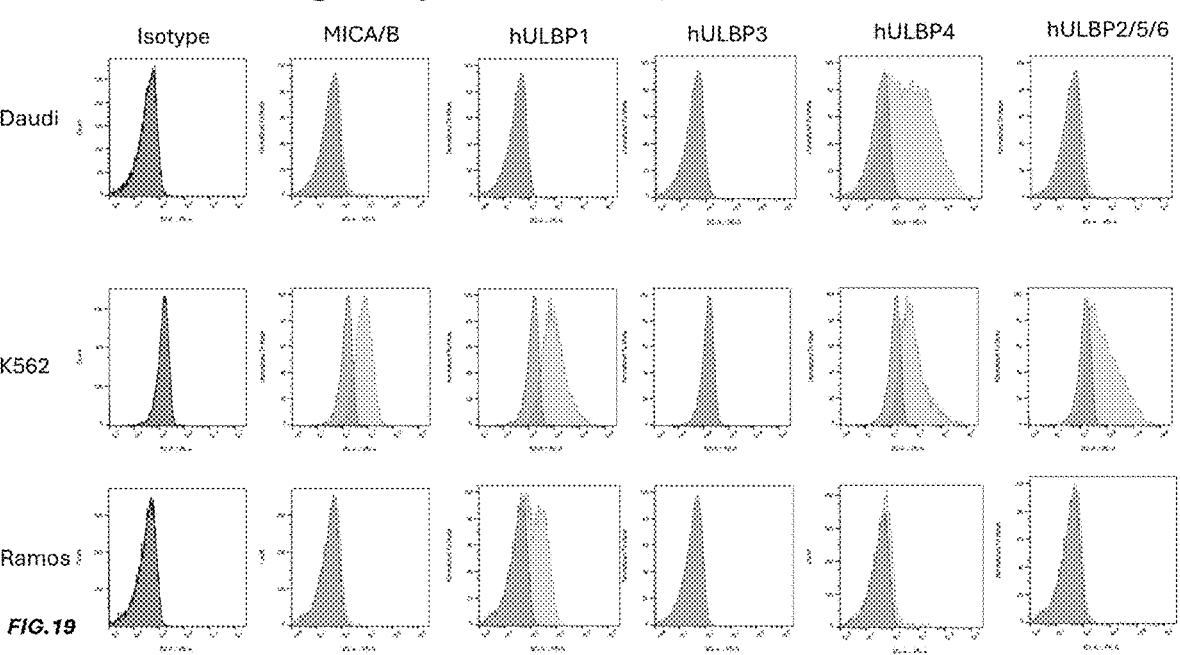
FIG. 19 depict exemplary NKG2D-Ligand expression on K562, Daudi, and Ramos cells.

The inventors knocked down the activating receptor NKG2D in NK92 cells and Clone 3B2 with the aim of reducing spontaneous cytotoxicity. Following depletion of the NKG2D-positive population, the knockout efficiency was validated, as illustrated in FIG. 18. FIG. 19 demonstrates expression of NKG2D ligand on different targets. K562 and Ramos were selected since they express NKG2D ligands.

Figure 20:
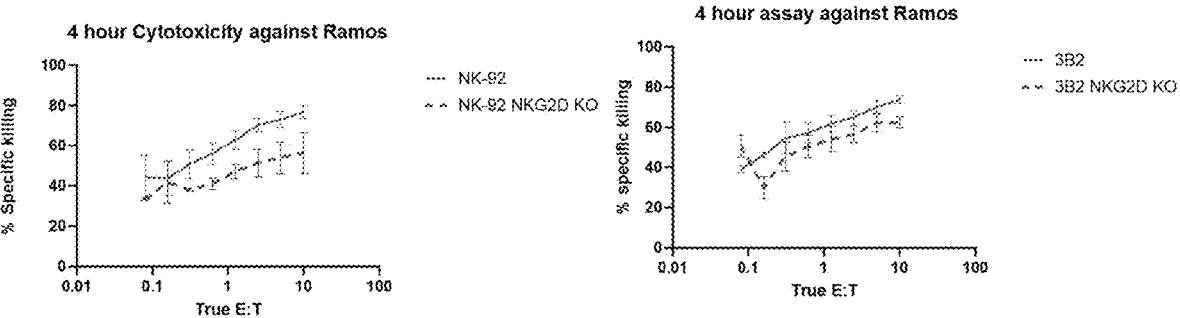
FIG. 20 depict exemplary cytotoxicity against Ramos cells upon NKG2D KO.
Figure 21:
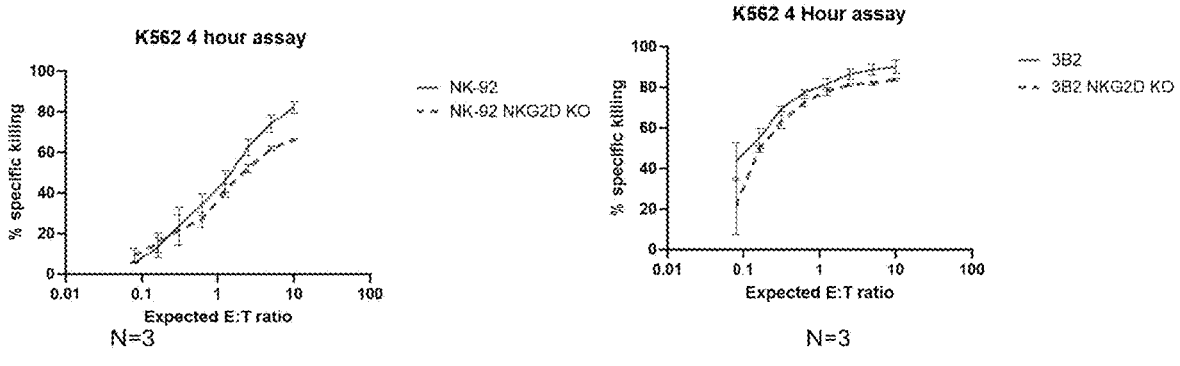
FIG. 21 depict exemplary cytotoxicity against K562 upon NKG2D KO.
Figure 23:
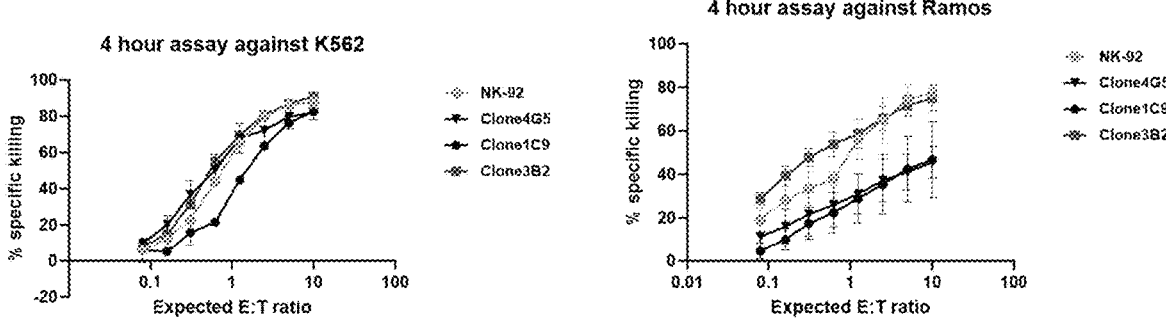
FIG. 23 depict exemplary cytotoxicity characterization against K562 and Ramos cells.

This targeted modification was designed to minimize background cytotoxicity while preserving ADCC functionality, optimizing these engineered clones for applications where reduced spontaneous activity is desirable. The inventors evaluated the cytotoxicity of the NKG2D-knockdown cells against the highly sensitive K562 and moderately sensitive Ramos cell lines (FIG. 20 and FIG. 21). The results showed a minor reduction in cytotoxicity against Ramos for NK92 cells following NKG2D depletion and no changes in K562 cytotoxicity. However, in clone 3B2, cytotoxicity levels remained unchanged, which illustrates that its killing mechanisms are less dependent on NKG2D signaling.

Example 6: Cytotoxicity Data

The inventors assessed the cytotoxicity of the engineered clones against a range of target cell lines, including the highly sensitive K562 as well as the moderately sensitive Ramos cells. This is illustrated in FIG. 19, FIG. 20, FIG. 21 and FIG. 22. This extensive characterization ensured that the clones maintained their functional properties across diverse target profiles. Notably, these clones retained their key characteristics before and after the freeze-thaw process, demonstrating their robustness.

ADCC was tested against SUP-B-15 expressing CD20 using Rituximab or control antibody Herceptin. It was found that ADCC is not affected upon NKG2D knockdown of haNK and Clone 3B2 (FIG. 22).

Following further evaluation, two clones were selected based on their distinct functional traits: Clone 1C9 was chosen for its lower cytotoxicity and high luciferase expression, while Clone 3B2 was selected for its cytotoxicity levels comparable to NK92 cells but with lower luciferase expression. These clones represent optimal candidates for different functional applications, providing flexibility based on therapeutic or research needs.

The lower cytotoxicity of Clone 1C9 results in a reduced background signal, leading to an improved signal-to-noise ratio.

Example 7: Methods

The materials and reagents used in the DNA electroporation for Knock-In of SFFV Promoter at CD16 Locus in NK-92 Cells are as follows:

Reagents are shown in Table 1:

TABLE 1

| Item | Vendor/Manufacturer | Catalog # |
|---|---|---|
| 100 µl Neon kit | Invitrogen | MKP10096T |
| R buffer | Invitrogen | MPK10096R |
| E2 buffer | Invitrogen | MPK10096E |
| Alt-R S.p. Cas9 V3 | IDT | 1081059 |
| Cas9 electroporation enhancer | IDT | 1075916 |
| D-PBS 1X | Gibco | 14190-144 |
| TE Buffer | Promega | V6321 |
| 10 mM Tris, 0.1 mM EDTA | | |
| HDR Enhancer | IDT | 10007921 |

Stock solutions are shown in Table 2:

TABLE 2

| Stock solution | Vendor |
|---|---|
| IL-2 | Prometheus |
| (ProleukinTM) | |
| 10,000 IU/uL | |

Reagents for media preparation are shown in Table 3:

TABLE 3

| Item | Manufacturer | Catalog # |
|---|---|---|
| X-VIVO 10 | Lonza | BP04-745Q |
| Human Male AB Serum, | Access | 515-HI |
| HI (Heat Inactivated) | Biologicals | |

Media used was: X VIVO 10+5% Human serum

Equipment is shown in Table 4:

TABLE 4

| Item (Model) | Manufacturer | Catalogue/ Model # | Serial # |
|---|---|---|---|
| Neon Electroporation | Invitrogen | MPK5000 | MP923577 | sgRNAs are shown in Table 5:

TABLE 5

| Item | Vendor | SgRNA sequence | Conc | Suspended in |
|------|--------|----------------|------|--------------|
| SgRNA AJ | IDT | ACCATAGAACAGGACCAGGA | 44uM | TE |
| SgRNA 1 | IDT | GCCGGGAGCAGGCGTGAGTG | 44uM | TE |

Cell Line: NK-92 cells, cultured in X-VIVO with 5% Human Serum and IL-2 (500 IU/mL).

Donor DNA: Donor Plasmid is designed to ensure efficient knock in of SFFV promoter at CD16 gene locus, plasmid is assembled by gene synthesis. It contains SFFV promoter flanked by CD16 homology arms, PAM site specific to sgRNA AJ is mutated to prevent cleavage of donor DNA when sgRNA AJ is electroporated. Flanking CD16 homology arm contains a unique sequence that allows sgRNA 1 to linearize plasmid inside the cell post electroporation. An exemplary Donor DNA construct design is shown in SEQ ID NO:6. In this sequence nt 1-23 represents the SgRNA 1 Sequence, nt 24-350 represents 5' homology arm with mutated PAM, nt 351-784 is the SFFV promoter, nt 785-1093 represents the 3' homology am, and nt 1094-1116 represents the SgRNA 1 Sequence. The presence of these different elements in the nucleotide sequence are important element for successful knock in, and the homology arms allow the SFFV promoter to be inserted precisely.

HDR Knock-In (SFFV Promoter Insertion): Maintain NK-92 cells at a density of $0.5-1\times10^6$ cells/mL in with IL-2 (500 IU/mL) in X VIVO 10+5% Human serum. Take volume of aNK cells equal to 4 million cells, Spin down at 300 g for 5 minutes, then aspirate off media. Add 5 mL of 1×D-PBS and repeat this step twice. Suspend the cells in R buffer 80 µl/4 million cells. Prepare Cas9-sgRNA complex for SgRNA AJ by mixing 3 µL Cas9 (62 µM stock)+2 µL of 1×PBS buffer per reaction; combine 5 ul of sgRNA AJ (44 µM) with 5 µl of above cas9 suspension-Incubate for 30 mins at Room temperature (RT). Prepare second Cas9-sgRNA complex by mixing 1.2 µl Cas9 (62 µM stock)+0.8 µL of 1×PBS buffer per reaction; combine 2 ul of sgRNA 1 (44 µM) with 2 µl of above cas9 suspension-Incubate for 30 mins at RT. Assemble electroporation mix by adding 14 µL of RNP complex, 4 µg of Donor template, electroporation enhancer was diluted to 10.8 µM in R buffer, cell suspension (4 million cells) in 80 µL, total volume 116 µL. Pipette in 100 µL of above cell mix very slowly without creating any bubbles using NEON 100 µl neon electroporation tips. Place pipette with electroporation tip in cuvette containing 3.5 ml electroporation buffer E. Electroporate using following parameters: 1600V, 10 ms, 3 pulses Resuspend cells in 4 ml pre-warmed in X VIVO 10+5% Human serum with HDR enhancer at 1 uM final concentration.

In some embodiments, the numbers expressing quantities of ingredients, properties such as concentration, reaction conditions, and so forth, used to describe and claim certain embodiments of the invention are to be understood as being modified in some instances by the term "about." As used herein, the terms "about" and "approximately", when referring to a specified, measurable value (such as a parameter, an amount, a temporal duration, and the like), is meant to encompass the specified value and variations of and from the specified value, such as variations of +/−10% or less, alternatively +/−5% or less, alternatively +/−1% or less, alternatively +/−0.1% or less of and from the specified value, insofar as such variations are appropriate to perform in the disclosed embodiments. Thus, the value to which the modifier "about" or "approximately" refers is itself also specifically disclosed. The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

---

Sequence Listing

---

SEQ ID NO: 1
SFFV Promoter sequence
GTAACGCCATTTTGCAAGGCATGGAAAAATACCAAACCAAGAATAGAGAAGTTCAGATCAAGGGC
GGGTACATGAAAATAGCTAACGTTGGGCCAAACAGGATATCTGCGGTGAGCAGTTTCGGCCCCGG
CCCGGGGCCAAGAACAGATGGTCACCGCAGTTTCGGCCCCGGCCCGAGGCCAAGAACAGATGGTC
CCCAGATATGGCCCAACCCTCAGCAGTTTCTTAAGACCCATCAGATGTTTCCAGGCTCCCCCAAGG
ACCTGAAATGACCCTGCGCCTTATTTGAATTAACCAATCAGCCTGCTTCTCGCTTCTGTTCGCGCGC
TTCTGCTTCCCGAGCTCTATAAAAGAGCTCACAACCCCTCACTCGGCGCGCCAGTCCTCCGATTGA
CTGAGTCGCCCGGATCCCAGTGTGGTGGTACGGGGCCACC SEQ ID NO: 2
CD16 low affinity (158F)
MWQLLLPTALLLLVSAGMRTEDLPKAVVFLEPQWYRVLEKDSVTLKCQGAYSPEDNSTQW
FHNESLISSQASSYFIDAATVDDSGEYRCQTNLSTLSDPVQLEVHIGWLLLQAPRWVFKE
EDPIHLRCHSWKNTALHKVTYLQNGKGRKYFHHNSDFYIPKATLKDSGSYFCRGLFGSKN
VSSETVNITITQGLAVSTISSFFPPGYQVSFCLVMVLLFAVDTGLYFSVKTNIRSSTRDW
KDHKFKWRKDPQDK SEQ ID NO: 3
CD16 high affinity (158V)
MWQLLLPTALLLLVSAGMRTEDLPKAVVFLEPQWYRVLEKDSVTLKCQGAYSPEDNSTQW
FHNESLISSQASSYFIDAATVDDSGEYRCQTNLSTLSDPVQLEVHIGWLLLQAPRWVFKE
EDPIHLRCHSWKNTALHKVTYLQNGKGRKYFHHNSDFYIPKATLKDSGSYFCRGLVGSKN
VSSETVNITITQGLAVSTISSFFPPGYQVSFCLVMVLLFAVDTGLYFSVKTNIRSSTRDW
KDHKFKWRKDPQDK SEQ ID NO: 4
IL-2
MYRMQLLSCIALSLALVTNSAPTSSSTKKTQLQLEHLLLDLQMILNGINNYKNPKLTRML
TFKFYMPKKATELKHLQCLEEELKPLEEVLNLAQSKNFHLRPRDLISNINVIVLELKGSE
TTFMCEYADETATIVEFLNRWITFCQSIISTLT SEQ ID NO: 5
ER-IL-2
MYRMQLLSCIALSLALVTNSAPTSSSTKKTQLQLEHLLLDLQMILNGINNYKNPKLTRML
TFKFYMPKKATELKHLQCLEEELKPLEEVLNLAQSKNFHLRPRDLISNINVIVLELKGSE
TTFMCEYADETATIVEFLNRWITFCQSIISTLTGSEKDEL SEQ ID NO: 6
Construct design
GCCGGGAGCAGGCGTGAGTGTGGGAAATGAAGGAAGCCCTCAGAGAATGCTCCTCCCACCTTGAAT
CTCATCCCCAGGGTCTCACTGTCCCATTCTTGGTGCTGGGTGGATCCAAATCCAGGAGATGGGGCAAGC
ATCCTGGGATGGCTGAGGGCACACTCTGGCAGATTCTGTGTGTGTGTCCTCAGATGCTCAGCCACAGACCTT
TGAGGGAGTAAAGGGGGCAGACCCACCCACCTTGCCTCCAGGCTCTTTAATTCCTGGTCCTGTTCTATG
GTGGGGCTCCCTTGCCAGACTTCAGACTGAGAAGTCAGATGAAGTTTCAAGAAAAGGAAATTGGTGGGTG
ACAGAGGTAACGCCATTTTGCAAGGCATGGAAAAATACCAAACCAAGAATAGAGAAGTTCAG
ATCAAGGGCGGGTACATGAAAATAGCTAACGTTGGGCCAAACAGGATATCTGCGGTGAGCA
GTTTCGGCCCCGGCCCGGGGCCAAGAACAGATGGTCACCGCAGTTTCGGCCCCGGCCCGAG
GCCAAGAACAGATGGTCCCCAGATATGGCCCAACCCTCAGCAGTTTCTTAAGACCCATCAGA
TGTTTCCAGGCTCCCCCAAGGACCTGAAATGACCCTGCGCCTTATTTGAATTAACCAATCAG
CCTGCTTCTCGCTTCTGTTCGCGCGCTTCTGCTTCCCGAGCTCTATAAAAGAGCTCACAACCC
CTCACTCGGCGCGCCAGTCCTCCGATTGACTGAGTCGCCCGGATCCCAGTGTGGTGGTACG
GGGCCACCATGGGTGGAGGGGCTGGGGAAAGGCTGTTTACTTCCTCCTGTCAGTCGGTTTGGTC
CCTTTAGGGCTCCGGATATCTTTGGTGACTTGTCCACTCCAGTGTGGCATCATGTGGCAGCTGCTCC
TCCCAACTGCTCTGCTACTTCTAGGTAAGTCAGGGTCTCCCTGGTTGAGGGAGAAGTTTGAGATGC
CTTGGGTTCAGCAGAGACCCCTTTTCAGGCTACGAATGAGACTCCCACGAAGGGATGGGACCCCTC
ACCACATCTATAGCTGTGGATTGAGCTCCTAGGACAAGCCAAGATGGGGCTAGGCCGGGAGCAG
GCGTGAGTGTGG

---

What is claimed is:

1. An isolated recombinant NK-92 cell that is natively heterozygous for CD16, comprising:

a native CD16 gene that is natively heterozygous for CD16, wherein the native CD16 gene has a CD16 158V allele and a CD16 158F allele;

a recombinant constitutive promotor sequence upstream of the native CD16 gene that is functionally in place of a native promotor sequence of the native CD16 gene;

wherein the recombinant promotor sequence is operably coupled to the native CD16 gene to thereby enable expression of the native CD16; and wherein the recombinant promoter sequence leads to detectable expression of the CD16 158V allele, but not the 158F allele.

2. The isolated recombinant NK-92 cell of claim 1, wherein the recombinant promotor sequence is a non-human promotor sequence.

3. The isolated recombinant NK-92 cell of claim 1, wherein the recombinant promotor sequence is a spleen focus forming virus (SFFV) promotor sequence.

4. The isolated recombinant NK-92 cell of claim 1, wherein the recombinant promotor sequence replaces an inactive native promotor sequence.

5. The isolated recombinant NK-92 cell of claim 1, wherein the NK-92 cell remain viable for at least 6 months and/or wherein the NK-92 cell express CD16 consistently for at least 6 months.

6. The isolated recombinant NK-92 cell of claim 1, wherein the recombinant NK-92 cell further comprises a recombinant nucleic acid that encodes an intracellularly retained cytokine.

7. The isolated recombinant NK-92 cell of claim 6, wherein the intracellularly retained cytokine is an IL-2 or er-IL-2.

8. The isolated recombinant NK-92 cell of claim 1, wherein the recombinant nucleic acid further encodes an antibiotic resistance gene and/or a reporter gene.

9. The isolated recombinant NK-92 cell of claim 1, wherein the recombinant NK-92 cell has antibody-dependent cellular cytotoxicity (ADCC) against a target cell expressing an antigen, and wherein the antigen is bound by an antibody that is bound to the CD16 expressed on the surface of the recombinant NK-92 cell.

10. The isolated recombinant NK-92 cell of claim 1, wherein the recombinant NK-92 cell, compared to a non-recombinant NK-92 cell, has a reduced signal-to-noise ratio for ADCC and/or reduced non-antibody-dependent cellular cytotoxicity (ADCC) cytotoxicity as compared to a non-recombinant NK-92 cell.

11. A method of testing an antibody, comprising:

providing a plurality of target cells expressing an antigen, providing a plurality of recombinant NK-92 cells of claim 1;

combining the target cells and the recombinant NK-92 cells with an antibody that binds to the antigen; and measuring ADCC against the target cells.

12. The method of claim 11, wherein the antibody is an IgG for therapy in human.

13. The method of claim 11, wherein a ratio of recombinant NK-92 cells to target cells is between 0.1:1 and 50:1.

14. The method of claim 11, wherein the method generates results that are more predictive than the same method using NK-92 cells expressing a transgene homozygous high-affinity CD16.

15. A method of making a recombinant NK-92 cell, comprising:

providing a NK-92 cell;

introducing to the NK-92 cell a recombinant constitutive promotor sequence upstream of a gene encoding a native CD16 allele to thereby make the recombinant NK-92 cell;

wherein the step of introducing the recombinant promotor sequence comprises functional replacement of a native promotor sequence of the native CD16 allele by homologous recombination with the recombinant promotor sequence;

wherein the recombinant promotor sequence is operably coupled to the native CD16 allele to thereby enable expression of the native CD16 allele; and wherein the recombinant promoter sequence leads to detectable expression of the CD16 158V allele, but not the 158F allele.

16. The method of claim 15, wherein the recombinant promotor sequence is a non-human promotor sequence.

17. The method of claim 15, wherein the recombinant promoter sequence is introduced to the NK-92 cell via electroporation.

* * * * *